(12) United States Patent
Wong et al.

(10) Patent No.: US 8,354,127 B2
(45) Date of Patent: Jan. 15, 2013

(54) **STRUCTURE AND BIOACTIVITY OF THE POLYSACCHARIDES AND OLIGOMERS IN MEDICINAL PLANT *DENDROBIUM HUOSHANENSE***

(75) Inventors: Chi-Huey Wong, La Jolla, CA (US); Wen-Bin Yang, Nankang (TW); Ting-Jen Cheng, Yung-He (TW); Yves Shang-Yi Hsieh, Auckland (NZ); Cheng Chien, Taipei (TW); Chih-Chien Lin, Taipei County (TW); Hao-Yu Wen, Kaohsiung (TW); Jim-Min Fang, Taipei (TW)

(73) Assignee: Academia Sinica, Taipei (TW)

( * ) Notice: Subject to any disclaimer, the term of this patent is extended or adjusted under 35 U.S.C. 154(b) by 716 days.

(21) Appl. No.: 12/378,263

(22) Filed: Feb. 12, 2009

(65) Prior Publication Data
US 2009/0270344 A1    Oct. 29, 2009

Related U.S. Application Data

(60) Provisional application No. 61/028,143, filed on Feb. 12, 2008.

(51) Int. Cl.
*A61K 36/00*    (2006.01)
*A61K 31/715*    (2006.01)

(52) U.S. Cl. .......................................... 424/725; 514/54
(58) Field of Classification Search .................. None
See application file for complete search history.

(56) References Cited

U.S. PATENT DOCUMENTS

| 2006/0064791 | P1 * | 3/2006 | Wang |
| 2007/0072247 | A1 * | 3/2007 | Wong et al. ............. 435/7.2 |
| 2008/0292644 | A1 * | 11/2008 | Hsieh et al. ............ 424/173.1 |

FOREIGN PATENT DOCUMENTS

| CN | 1726993 | * | 2/2006 |
| CN | 1871940 | * | 12/2006 |

OTHER PUBLICATIONS

Zha et al. Pharm. Biol., Jan. 2007, vol. 45, No. 1, pp. 71-76.*
Zha et al. Shipin Kexue (Beijing, China). 2005. vol. 26, No. 4, pp. 41-44, CAPLUS Abstract enclosed.*
Zha et al. Carbohydrate Polymers. 2007. vol. 69, pp. 86-93.*

* cited by examiner

*Primary Examiner* — Christopher R. Tate
(74) *Attorney, Agent, or Firm* — Eckman Basu LLP

(57) ABSTRACT

Compositions and methods are disclosed relating to use of fractions, polysaccharides, and oligosaccharides of *Dendrobium huoshanense*. The fractions, polysaccharides, and oligosaccharides are able to effect an increase in beneficial cytokines and chemokines.

11 Claims, 25 Drawing Sheets
(5 of 25 Drawing Sheet(s) Filed in Color)

STRUCTURE AND BIOACTIVITY OF THE POLYSACCHARIDES AND OLIGOMERS IN MEDICINAL PLANT *DENDROBIUM HUOSHANENSE*

RELATED APPLICATIONS

This application claims the priority of and incorporates by reference U.S. Provisional Patent Application Ser. No. 61/028,143, filed Feb. 12, 2008, entitled "Structure and Bioactivity of the Polysaccharides in Medicinal Plant *Dendrobium huoshanense*."

BACKGROUND

This disclosure relates to the determination of the polysaccharides found in *Dendrobium houshanense* and the effect of administration of the polysaccharides to trigger immunomodulatory activity, including the up regulation of beneficial cytokines.

*Dendrobium huoshanense* is a precious and endangered medicinal plant that originated in China. In this study, detailed structures of the polysaccharides extracted from the leaf and stem cell walls and mucilage of *D. huoshanense* are determined by using various techniques, including chromatographic, spectroscopic, chemical and enzymatic methods. The composition of monosaccharides and their linkages in the cell wall and mucilage were deduced. In addition to the previously reported mannose, glucose and galactose, new monosaccharide constituents of rhamnose, fucose, arabinose, xylose, galacturonic acid, glucuronic acid, 4-O-methylglucouronic acid and 2-O-acetylmannose are firstly found in *D. huoshanense*. The pectic fractions of leaf and stem are found to contain mostly homogalacturonan (HGA) and galactomannan, with a smaller proportion of rhamnogalacturonan (RG). The alkali extractable fractions are mainly composed of glucuronoarabinoxylans (GAXs), fucosylated xyloglucans (XGs) and glucomannan. In contrast, the mucilage polysaccharide extracted from stems and leaves is composed of 2- and 3-O-acetyl glucomannan. The mucilage polysaccharide exhibits specific functions in activating murine splenocytes to produce several cytokines including IFN-γ, IL-10, IL-6, and IL-1α, as well as hematopoietic growth factors GM-CSF and G-CSF. However, the deacetylated mucilage obtained from an alkaline treatment failed to induce cytokine production.

The extract of mucilage was further fractionated by chromatography on anion-exchange DEAE-cellulose and Sephacryl size-exclusion. The bioactive polysaccharide fraction B with an average molecular weight of ~10 KDa is composed of β-(1→4)glucomannan having partial acetylation at the 2- and 3-positions of mannosides. The linkages of β-(1→4)-D-Glcp and β-(1→4)-D-Manp were elucidated by NOE spectrum and enzymatic methods. The chemical shifts of individual protons and carbons were assigned by using a series of 2D NMR spectroscopic techniques. This is the first study that provides clear evidence for the structure and activity relationship of the polysaccharides in *D. huoshanense*.

Moreover, the fragments of oligosaccharide from *Dendrobium huoshanense* obtained by either acid hydrolysis or enzyme digestion, with or without chemical modification, also induce expression of beneficial protein, such as G-CSF that shows potential application of therapeutic uses.

Based on the above-mentioned discovery, bioactive mannose oligomers are prepared from high-molecular-weight mannans by using a combination of methods, including acid hydrolysis, enzyme digestion, extraction, dialysis, chromatography and chemical modification. The oligosaccharide containing six or more units of mannosides can induce expression of beneficial proteins, such as cytokines and growth factors in time- and dose-dependent manner.

SUMMARY

Compositions and methods are disclosed relating to use of fractions, polysaccharides, and oligosaccharides of *Dendrobium huoshanense*. The fractions, polysaccharides, and oligosaccharides are able to effect an increase in beneficial cytokines and chemokines.

According to a feature of the present disclosure, a composition is disclosed comprising an extract of *D. huoshanense*. The extract comprises at least fraction B and at least one polysaccharide is administered to upregulate beneficial proteins.

According to a feature of the present disclosure, a method is disclosed comprising isolating at least one polysaccharide from *D. huoshanense*, preparing a preparation comprising the at least one polysaccharide and a pharmaceutically acceptable carrier; and providing the preparation for administration to an animal to upregulate beneficial proteins in the animal.

According to a feature of the present disclosure, a composition is disclosed comprising at least fraction B of *D. huoshanense* and a pharmaceutically acceptable carrier.

According to a feature of the present disclosure, a composition is disclosed comprising a β-(1→4)glucomannan having partial acetylation at 2- and 3-positions of mannosides and a pharmaceutically acceptable carrier.

According to a feature of the present disclosure, A method is disclosed comprising using hemicellulase in the production of an extract of *D. huosanense* having bioactive mannose oligomers.

DRAWINGS

The patent or application file contains at least one drawing executed in color. Copies of this patent or patent application publication with color drawing(s) will be provided by the Office upon request and payment of the necessary fee. The above-mentioned features and objects of the present disclosure will become more apparent with reference to the following description taken in conjunction with the accompanying drawings wherein like reference numerals denote like elements and in which.

DETAILED DESCRIPTION

In the following detailed description of implementations of the invention, reference is made to the accompanying drawings in which like references indicate similar elements, and in which is shown by way of illustration specific implementations in which the invention may be practiced. These implementations are described in sufficient detail to enable those skilled in the art to practice the invention, and it is to be understood that other implementations may be utilized and that logical, mechanical, biological, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction and shall not indicate an exclusive disjunction unless expressly indicated as such or notated as "xor."

The inventors have discovered that the polysaccharides in the cell wall and stem of *D. huoshanense* are mainly composed of monosaccharides Xyl, Ara, Man, Glc, Gal, and GalA, along with small proportions of Rha, Fuc, GlcA, and 4-O-methyl GalA. The glycosyl linkages of these monosaccharide residues were determined to give an insight into the structure of polysaccharides. The pectic fractions from the CDTA extraction of the cell wall and stem polysaccharides were found to contain galactomannans, galactans, arabinans, and rhamnogalacturonans I, whereas heteroxylan, glucuronoarabinoxylans, and xyloglucans existed in the KOH fractions. Some xyloglucans are modified with terminal fucose and Gal side-chain. The stem mucilage contains glucomannan in β-(1→4)-D-Glcp and β-(1→4)-D-Manp linkages with partial acetylated mannosides at the 2- and 3-position. The mucilage polysaccharide exhibited specific functions in murine splenocytes. The mucilage induced several cytokines, including IFN-γ, IL-10, IL-6, and IL-1α, and hematopoietic growth factors GM-CSF and G-CSF. However, the deacetylated mucilage obtained from an alkaline treatment failed to induce cytokine production.

The extract of mucilage was further fractionated by chromatography on anion-exchange DEAE-cellulose and Sephacryl size-exclusion. The bioactive polysaccharide fraction B was determined to have an average molecular weight of ~10 KDa, and its composition and structure were rigorously determined by a combination of chemical, enzymatic, and spectroscopic methods. This is the first study that provides clear evidence for the structure and activity relationship of the polysaccharide in *D. huoshanense*.

Figure 1:
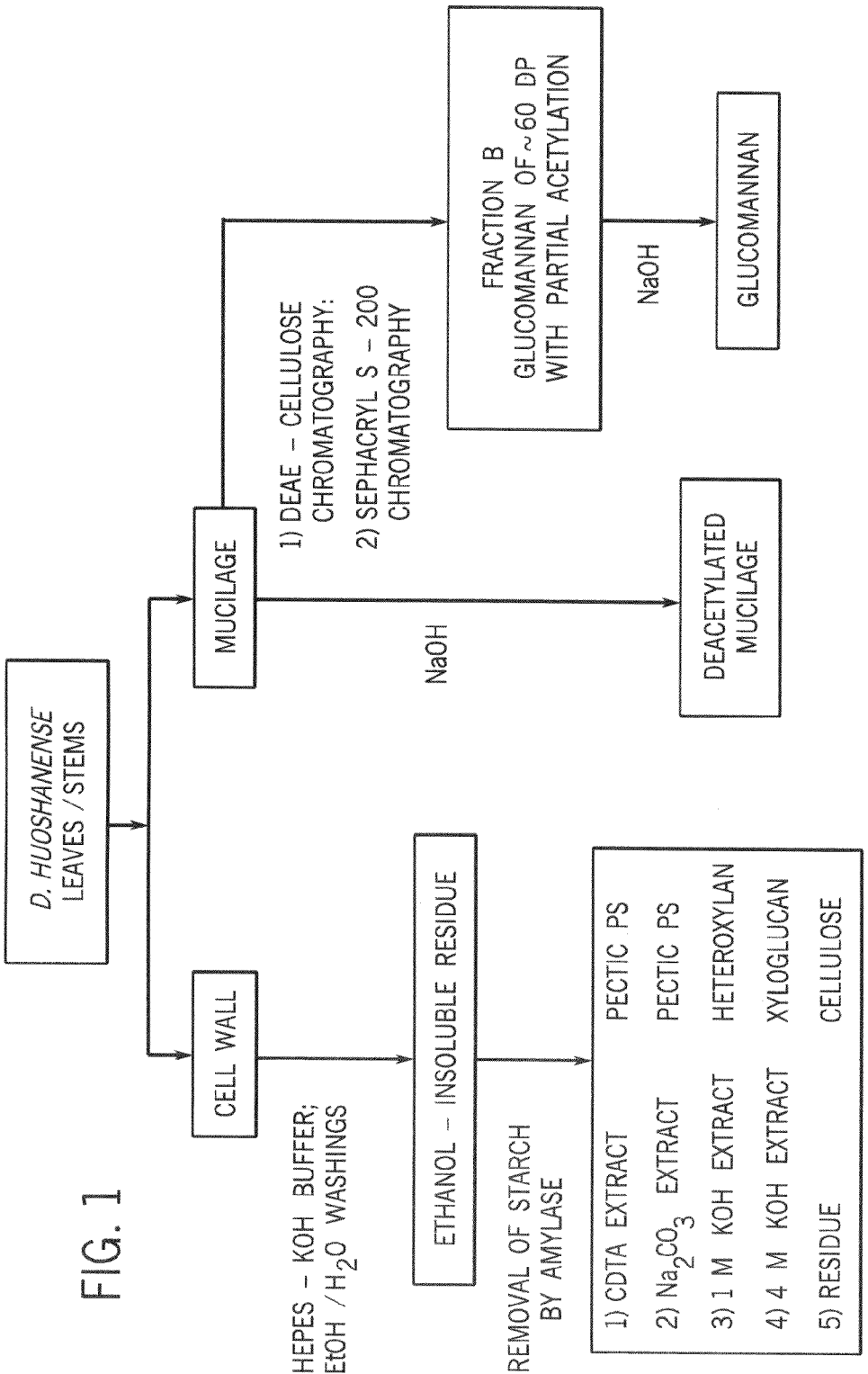
FIG. 1 is an illustration showing implementations of the isolation of polysaccharides from *D. huoshanense*.

The plant material of *D. huoshanense* was obtained from Yuen-Foong-Yu Biotech Co. in Taiwan. The isolation of polysaccharides from *D. huoshanense* is illustrated in FIG. 1. The tissues containing non-lignified primary cell walls were collected from leaves and stems at 4° C. The alcohol-insoluble residue (AIR) was treated with porcine pancreatic amylase to remove starch. The de-starched cell walls were fractionated by a sequence of extraction using CDTA (cyclohexane-1,2-diamine tetraacetate), $Na_2CO_3$, 1 M KOH, and 4 M KOH. The remaining insoluble residue was accounted for the α-cellulose fraction. As shown by the test with potassium iodide, the mucilage polysaccharides collected from leaves and stems did not contain any starch granules.

According to implementations, the inventors discovered that the backbone of oligosaccharides from *Dendrobium huoshanense* contains glucose and mannose with β-1,4-linkage in 1:10 ratio. When cells are treated with the oligosaccharides from *Dendrobium huoshanense*, induction/expression of beneficial protein is observed.

The fragments of *Dendrobium huoshanense* may be produced according to implementations disclosed herein. For example, the fragments of oligosaccharide from *Dendrobium huoshanense* are obtained by acid hydrolysis or enzyme digestion, as illustrated by the flow diagram in FIG. 2. The resulting *Dendrobium huoshanense* fragments (with or without chemical modification) are able to induce expression of beneficial protein, such as G-CSF as illustrated in Table 1.

TABLE 1

Activities of various preparations of oligo- and polysaccharides[a] from *Dendrobium huoshanense*

| Entry | Sample | Percentage of acetylation (%)[b] | Description[c] | Increased G-CSF expression[d] |
|---|---|---|---|---|
| 1 | DH001 | | DP > 11 | + |
| 2 | DH002 | 12-22 | DP = 3-9 | + |
| 3 | DH003 | 12-23 | DP = 2-7 | + |
| 4 | DH004 | 6-13 | DP = 2-6 | − |
| 5 | DH005 | 12-22 | DP = 2-4 | − |
| 6 | DH006 | 17 | | + |
| 7 | DH007 | 0 | | − |
| 8 | DH014 | 0 | DP = 7-9 | + |
| 9 | DH015 | 12-27 | DP = 4-11 | + |
| 10 | DH016 | 12-20 | DP = 3-7 | + |
| 11 | DH017 | 12-22 | DP = 3-8 | + |
| 12 | DH018 | 15 | | ± |
| 13 | DH019 | 18 | | ± |
| 14 | DH020 | 0 | | ± |
| 15 | DH021 | 12 | | + |
| 16 | DH022 | 14 | | + |
| 17 | DH023 | 0 | | − |

[a]Samples are prepared as shown in Fig. 1.
[b]The percentage of acetylation was estimated by $^1$H NMR analysis.
[c]The degree of polymerization (DP) was deduced by the observed signals in MALDI-MS analysis.
[d]+: significant expression of G-CSF; −: no induced expression of G-CSF; ±: the expression level is only slightly higher than the control cells, no clear answer.

Figure 3:
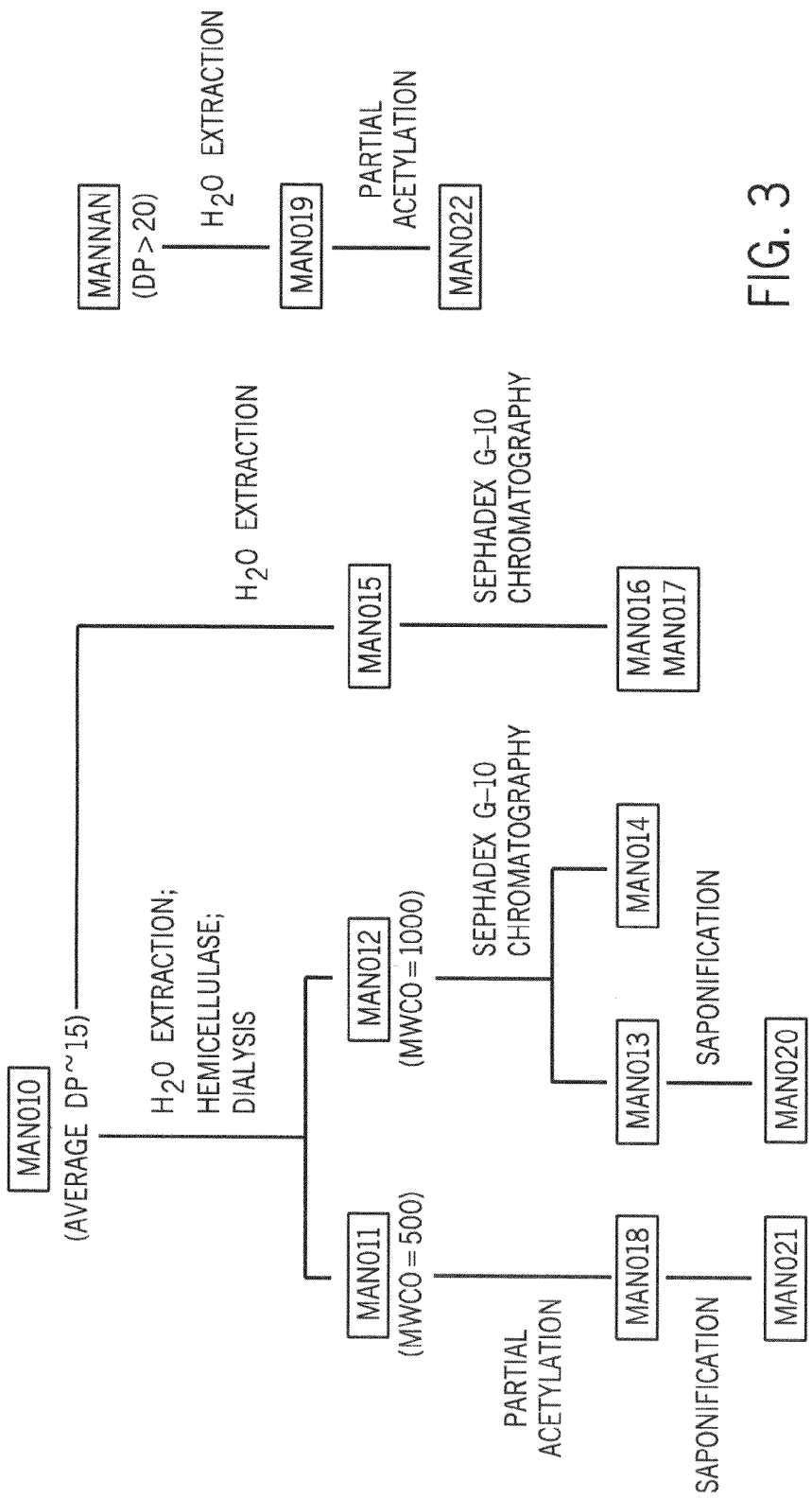
FIG. 3 is an illustration showing implementations of the preparation of mannose oligomers Man001-Man022 for activity analysis.

According to implementations, high-molecular-weight mannans are degradable by a combination of methods (FIG. 3). For example, acid hydrolysis, enzyme digestion, extraction, dialysis, chromatography and chemical modification, all are able to produce bioactive mannose oligomers (Table 2).

TABLE 2

Activities of various preparations of mannan and mannose oligomers[a]

| Entry | Sample | Percentage of acetylation (%)[b] | Description[c] | Increased G-CSF expression[d] |
|---|---|---|---|---|
| 1 | Man001 | 0 | (Man)$_5$ | − |
| 2 | Man002 | 100 | (Man)$_5$ | − |
| 3 | Man003 | 0 | 66% (Man)$_6$ + 34% (Man)$_n$ (n ≧ 7) | + |
| 4 | Man004 | 100 | Peracetylation product of Man003 | − |
| 5 | Man005 | 10 | 10% acetylation product of Man003 | ± |
| 6 | Man006 | 20 | 20% acetylation product of Man003 | ± |
| 7 | Man007 | 30 | 30% acetylation product of Man003 | ± |
| 8 | Man008 | 40 | 40% acetylation product of Man003 | ± |
| 9 | Man009 | 50 | 50% acetylation product of Man003 | ± |
| 10 | Man010 | 0 | Average DP ~15 | − |
| 11 | Man011 | 0 | DP = 3-9 | + |
| 12 | Man012 | 0 | DP = 5-10 | + |
| 13 | Man013 | 0 | DP = 5-10 | ++ |
| 14 | Man014 | 0 | DP = 5-10 | + |
| 15 | Man015 | 0 | DP = 3-19 | − |
| 16 | Man016 | 0 | DP = 3-19 | − |
| 17 | Man017 | 0 | DP = 2-15 | − |
| 18 | Man018 | 25 | DP = 3-9 | + |
| 19 | Man019 | 0 | DP > 20 | − |
| 20 | Man020 | 0 | DP = 5-10 | + |
| 21 | Man021 | 0 | DP = 3-9 | − |
| 22 | Man022 | 20 | DP > 20 | − |

[a]Varying mannose oligomers were obtained by degradation of high-molecular-weight mannans (see FIG. 2).
[b]The percentage of acetylation was based on the stoichiometry of acetylating agent, and estimated by MS and $^1$H NMR analyses of the acetylation product.
[c]The degree of polymerization (DP) was estimated by the observed signals in MALDI-MS analysis.
[d]++: expression of G-CSF higher than *Denbrobium* polysaccharide (DHPS); +: significant expression of G-CSF; −: no induced expression of G-CSF; ±: the expression level is only slightly higher than the control cells, no clear answer.

Figure 6:
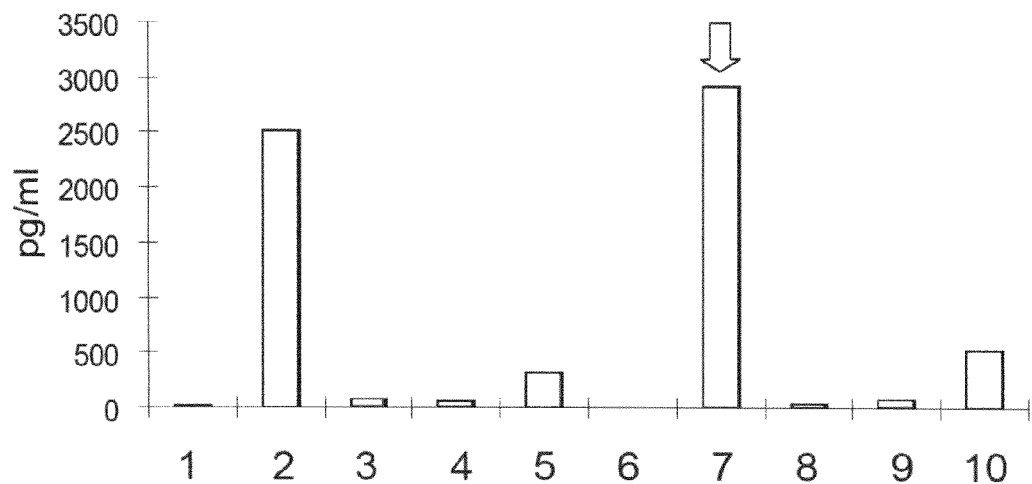
FIG. 6 is a graph of illustrative data of implementations of assessments of G-CSF expression of the protein level.
Figure 7:
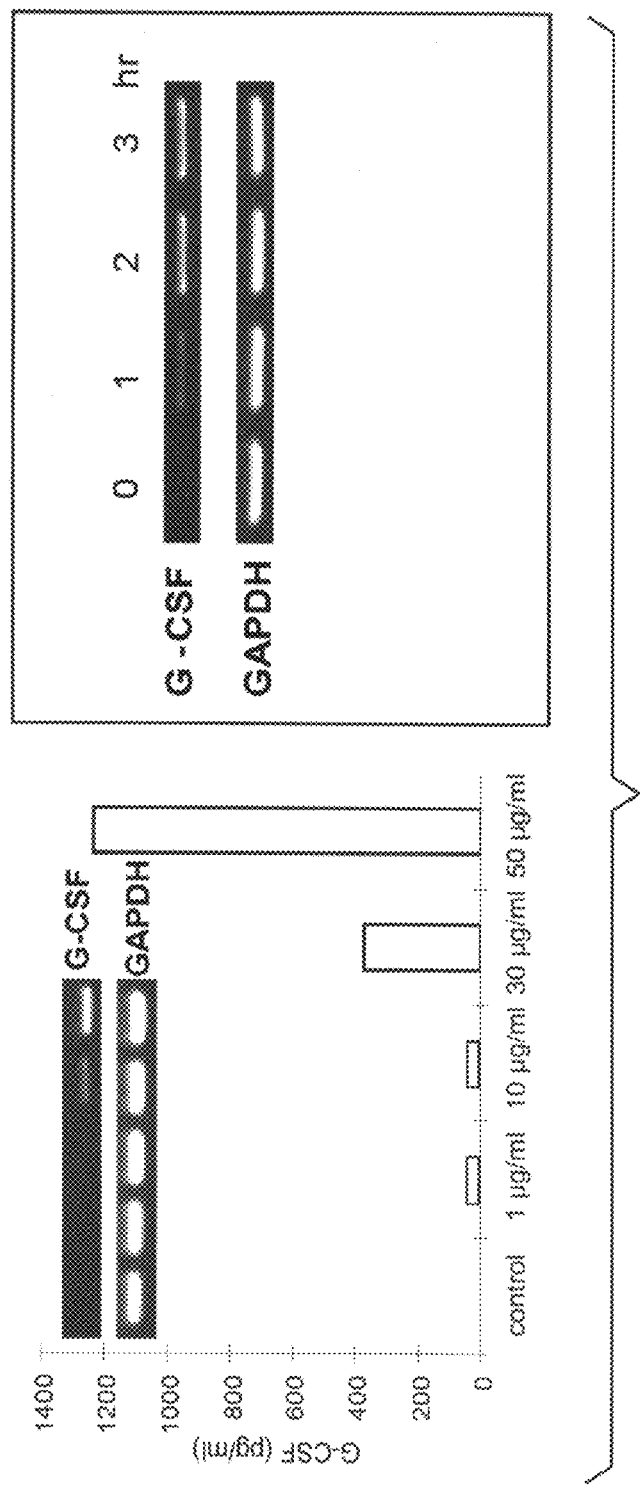
FIG. 7 are graphs of illustrative data of implementations of assessments of the dose- and time-dependent response of a mannose oligomer on the production of G-CSF.

According to implementations, an oligosaccharide containing six or more units of mannosides, for example, in β-1,4-linkage, with or without acetylation, was shown to induce expression of beneficial proteins, such as G-CSF (Table 2). Additionally, according to implementations, an oligosaccharide containing six or more units of mannosides can induce expression of beneficial proteins, such as cytokines and growth factors, as illustrated in (FIGS. 4-8), in a time- or dose-dependent manner, as illustrated in (FIG. 7).

Figure 8:
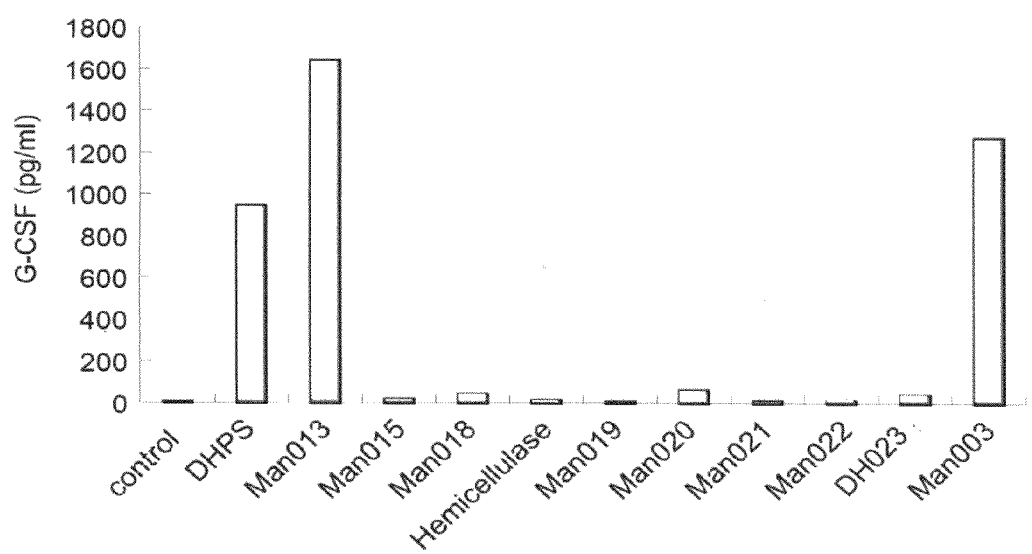
FIG. 8 is a graph of illustrative data of implementations of assessments of G-CSF expression of the protein level.

Moreover, according to implementations, a mannose oligomer obtained from a high-molecular-weight mannan by enzymatic degradation, dialysis, and chromatography showed a potent activity to induce expression of beneficial proteins, such as G-CSF, as illustrated in FIG. 8. According to implementations, hemicellulase is an effective enzyme for preparation of the bioactive mannose oligomers. Artisans will know and recognize equivalent enzymes having activity similar to hemicellulase to accomplish the same or similar results.

The activity of a polysaccharide prepared from *D. huoshanense* (DHPS) (see FIG. 2), with respect to inducing expression of beneficial proteins such as colony-stimulating factors may be applied in various ways. For example and according to implementations, granulocyte colony-stimulating factor (G-CSF) is a hematopoietic growth factor named for its role in the proliferation and differentiation of cells of the myeloic lineage. Administration of G-CSF mobilized hematopoietic stem cells (HSCs) from the bone marrow into the peripheral blood, thereby becoming crucial for the adoption of autologous peripheral blood stem cell transplantation in clinical practice. Additionally, G-CSF plays an important role in the basal regulation of neutrophil production, can rescue the memory impairment of animal models of Alzheimer's disease, or has potential therapeutic applications in autoimmune diseases and neurological disorders. G-CSF or combinatorial cytokine therapies have been found to result in myocardial homing of mobilized bone marrow cells, repair of the infracted myocardium, and improvement in left ventricular structural and functional parameters as well as survival.

G-CSF and its receptor likely function as an autocrine adaptive system within the central nervous system. Growth factors such as G-CSF and granulocyte macrophage colony-stimulating factor (GM-CSF) improves the hematologic tolerance of dose-intense combination-chemotherapy regimens. Granulopoiesis-stimulating factors such as granulocyte-colony-stimulating factor (G-CSF) and granulocyte-macrophage-colony-stimulating factor (GM-CSF), also increase the body's production of white blood cells, which in turn can reduce the risk of infection in people receiving chemotherapy for lymphoma.

According to implementations, this application expressly contemplates use of the active oligosaccharide from *D. huoshanense* in oral or injectable pharmaceutical compositions, for example. Similarly, the active mannose oligomers can be orally administered or by injection.

Monosaccharide Composition of Cell Wall

The cell-wall AIR preparation and individual fractions were subjected to hydrolysis with trifluoroacetic acid to release monosaccharides, which were subsequently reduced by $NaBH_4$ and acetylated by $Ac_2O$ to give the corresponding alditol peracetates. The composition of neutral monosaccharides correlated with that of alditol peracetates as determined by the GC-MS analysis (Table 3). The major constituents in the primary non-lignified cell walls of leaves were Ara, Man, Glc, and Gal, with small proportions of Xyl, Rha, and Fuc. On the other hand, the primary cell walls of stems contained mainly Xyl, Glc, Man, and Gal, small proportions of Ara and Rha, and a trace amount of Fuc. It was noted that greater proportion of Xyl was found in stem (28 mol %) than in leaf (7 mol %) cell-wall hydrolysates, but smaller proportion of Ara in stem (9 mol %) than in leaf (22 mol %). The uronic acid contents in the cell-wall preparations of leaves and stems were 11% and 4%, respectively. Three uronic acids, galacturonic acid (GalA), glucuronic acid (GlcA), and 4-O-methyl glucuronic acid (Me-GlcA) were found, with GalA predominating (75-87%).

The AIR of cell-wall preparation was further extracted with CDTA, $Na_2CO_3$ (+25 mM $NaBH_4$), 1 M KOH (+25 mM $NaBH_4$) and 4 M KOH (+25 mM $NaBH_4$) to give the corresponding fractions along with a residue of α-cellulose. The compositions of neutral monosaccharides and uronic acids of these fractions are shown in Table 3.

TABLE 3

Composition of neutral monosaccharides and uronic acids in cell walls and individual fractions from the leaves and stems of *D. huoshanense*.

| | Neutral monosaccharides[a] | | | | | | | | Uronic acids[a] | | | |
|---|---|---|---|---|---|---|---|---|---|---|---|---|
| | T[b] | Rha | Fuc | Ara | Xyl | Man | Gal | Glc | T[b] | GalA | GlcA | MeGlcA |
| Leaves | | | | | | | | | | | | |
| AIR[c] | 89 | 3 | 3 | 22 | 7 | 21 | 13 | 20 | 11 | 10 | tr[e] | 1 |
| CDTA[d] | 82 | 3 | tr[e] | 25 | tr[e] | 35 | 13 | 4 | 18 | 18 | tr[e] | tr[e] |
| $Na_2CO_3$[f] | 91 | tr[e] | — | 23 | 6 | 18 | 34 | 10 | 9 | 9 | tr[e] | tr[e] |
| 1 M KOH[g] | 89 | — | 2 | 17 | 28 | 20 | 9 | 13 | 5 | tr[e] | 4 | 1 |
| 4 M KOH[h] | 78 | — | 6 | 5 | 17 | 10 | 12 | 28 | 4 | 1 | 2 | 1 |
| Stems | | | | | | | | | | | | |
| AIR | 96 | 1 | tr[e] | 9 | 28 | 19 | 11 | 29 | 4 | 3 | tr[e] | 1 |
| CDTA | 73 | tr[e] | tr[e] | 11 | tr[e] | 27 | 28 | 5 | 27 | 23 | tr[e] | 4 |
| $Na_2CO_3$ | 76 | 1 | tr[e] | 27 | 3 | 7 | 31 | 8 | 24 | 23 | tr[e] | 1 |
| 1 M KOH | 94 | — | — | 1 | 65 | tr[e] | 19 | 9 | 6 | 2 | tr[e] | 4 |
| 4 M KOH | 94 | — | 2 | 3 | 24 | 14 | 10 | 41 | 6 | 3 | 1 | 2 |

[a]Composition in mol % as average of duplicate determinations.
[b]Total content in mol %.
[c]Alcohol insoluble residue.
[d]The fraction obtained by extraction with trans-cyclohexane-1,2-diamine-tetraacetate.
[e]Trace amount (<0.5%).
[f]The fraction obtained by extraction with $Na_2CO_3$ + 25 mM $NaBH_4$.
[g]The fraction obtained by extraction with 1 M KOH + 25 mM $NaBH_4$.
[h]The fraction obtained by extraction with 4 M KOH + 25 mM $NaBH_4$.

Both the CDTA and $Na_2CO_3$ fractions from leaf and stem cell-wall preparations contained large proportions of Man, Gal, and Ara. Much greater amounts of Xyl existed in the 1 M KOH fractions of leaf (28 mol %) and stem (65 mol %) than in the CDTA and $Na_2CO_3$ fractions. Glucose was the major component in the 4 M KOH fractions of leaf (28 mol %) and stem (41 mol %). Three uronic acids were found with galacturonic acid (GalA) predominated in the CDTA and $Na_2CO_3$ fractions. In the 1 M and 4M KOH fractions of leaves, the content of glucuronic acid (GlcA) was higher than 4-O-methyl GlcA (MeGlcA), while the opposite was observed in stems.

GalA is characteristic of the presence of pectic polysaccharides, and the presence of both GlcA and 4-O-methyl GlcA is typical in heteroxylans. Results indicated that a high proportion of pectic polysaccharides existed in both the CDTA and $Na_2CO_3$ fractions, whereas a large amount of heteroxylan existed in the KOH fractions.

Linkage Analysis of the Cell-wall Fractions

Glycosyl linkages between monosaccharide residues provided information for the structure of polysaccharides. The glycosyl linkages of the cell-wall fractions in leaves and stems of *D. huoshanense* are summarized in Table 4.

TABLE 4

Glycosyl linkage composition in the cell wall fractions of *D. huoshanense*.

| Glycosyl linkage | Leaves | | | | Stems | | | |
|---|---|---|---|---|---|---|---|---|
| | CDTA | Na$_2$CO$_3$ | 1 M KOH | 4 M KOH | CDTA | Na$_2$CO$_3$ | 1 M KOH | 4 M KOH |
| 2-Rhap | 2.6 | 1.4 | 0.2 | — | 2.6 | — | — | — |
| t-Fucp | 1.3 | — | 0.1 | 1.4 | — | — | 0.1 | 0.3 |
| t-Araf | 9.3 | 6.7 | 11.3 | 1.4 | 7.1 | 13.1 | 7.4 | 3.5 |
| 2-Araf | 2.3 | 2.1 | 3.9 | — | 2.3 | 2.3 | 1.5 | — |
| 3,5-Araf | 1.9 | 5.9 | — | — | 6.6 | 8.0 | — | — |
| 5-Araf | 5.1 | 5.7 | — | — | 2.8 | 3.2 | — | — |
| t-Xylp | 2.6 | 1.5 | 22.2 | 4.0 | 4.3 | 4.9 | 8.8 | 2.6 |
| 2-Xylp | — | — | 0.5 | 2.6 | — | — | 2.2 | 4.3 |
| 3-Xylp | — | — | 1.6 | 1.8 | — | — | 4.5 | 0.7 |
| 4-Xylp | 1.8 | 2.2 | 14.7 | 11.9 | 0.8 | 1.9 | 30.0 | 13.0 |
| 2,4-Xylp | — | — | 1.5 | — | — | — | 3.2 | — |
| 3,4-Xylp | — | 3.2 | 3.2 | 2.0 | — | — | 4.8 | 2.7 |
| t-Galp | 8.2 | 13.5 | 0.9 | 4.0 | 5.4 | 8.5 | 5.7 | 7.3 |
| 4-Galp | 7.0 | 23.5 | 10.7 | 2.2 | 10.1 | 34.4 | 13.4 | 4.1 |
| 6-Galp | 4.5 | 0.7 | — | — | 3.2 | — | — | — |
| 2-Galp | — | — | — | 4.3 | — | — | — | 7.4 |
| t-Glcp | 0.6 | 1.6 | 2.8 | 1.2 | 5.2 | 4.2 | 1.6 | 1.9 |
| 2,3-Glcp | 0.5 | — | — | 1.0 | — | — | — | 4.1 |
| 3-Glcp | — | — | — | — | — | — | — | 0.8 |
| 3,4-Glcp | — | — | — | 3.2 | — | — | — | 6.0 |
| 4-Glcp | 7.3 | 7.4 | 6.1 | 39.0 | 7.7 | 7.0 | 6.4 | 18.9 |
| 4,6-Glcp | — | — | 3.3 | 8.4 | — | — | 9.8 | 8.9 |
| 4-Manp | 26.3 | 14.1 | 17.0 | 10.8 | 20.9 | 9.4 | 0.6 | 13.5 |
| 4,6-Manp | 18.7 | 10.5 | — | 0.8 | 21.0 | 3.1 | — | — |

$^a$The polysaccharide sample was subjected to a sequence of permethylation, hydrolysis, reduction, and peracetylation, and the glycosyl linkage was deuced from the GC-MS analysis of the resulting methylated alditol acetates. The data in mole percentage (mol %) are average of duplicate determinations.

In the CDTA fractions of leaves and stems cell-wall preparations, mannose in the form of 4-Manp and 4,6-Manp was most abundant. Along with the high proportions of t-Galf, 4-Galf, t-Araf, and 5-Araf, the composition of CDTA fractions was characterized by galactomannans, galactans, and arabinans (where "t" represents the terminal position of sugars at the non-reducing end). The small amount of 2-Rhap found in the CDTA fractions might be attributed to the presence of rhamnogalacturonans I (RG I).

The glycosyl-linkage compositions in the Na$_2$CO$_3$ fractions were similar to those in CDTA fractions, albeit with much greater proportions of 4-Galp and smaller proportions of 4-Manp and 4,6-Manp. Galactomannans were observed in the pectic fractions (CDTA+Na$_2$CO$_3$ extractions) of *D. huoshanense* cell-wall preparations. The galactomannan of *Leucaena leucocephala* can form complexes with divalent metal ions, e.g., Co$^{2+}$, Mn$^{2+}$, Ni$^{2+}$ and Zn$^{2+}$. Thus, it is possible that the leaf and stem cell-wall preparations of *D. huoshanense* might contain the complexes of galactomannan-metal ions, which was subsequently extracted by CDTA and Na$_2$CO$_3$ treatments and therefore confirmed.

High proportions of t-Xylp, 4-Xylp, and t-Araf glycosyl linkages were observed in the 1 M KOH fractions of primary cell-wall preparations of *D. huoshanense*. Along with the presence of GlcA and 4-O-methyl GlcA in high proportions (see Table 3), trace amounts of glucuronoarabinoxylans (GAXs) were observed. Unbranched 4-Xylp linkage predominated in the GAXs of *D. huoshanense*. In comparison, the GAXs found in the primary cell walls of maize (*Zea mays*, Poaceae) and pineapple (*Ananas comosus*, Bromeliaceae) contain high proportions of branched 2,4-Xylp and 3,4-Xylp glycosyl linkages. Furthermore, the GAXs in *D. huoshanense* differed from that in grasses and pineapple by having no ester-linked hydroxycinnamic acid.

The presence of xyloglucans in the KOH fractions of leaves and stems was indicated by the predominant glycosyl linkages of t-Xylp, 2-Xylp, 4-Glcp and 4,6-Glcp. The presence of t-Fucp indicated that the xyloglucans might be fucosylated. A large amount of 4-Manp glycosyl linkage might be attributable to mannans or glucomannans.

Analysis of the Pectic Polysaccharides in CDTA Fractions

The above-mentioned analyses of the uronic acid composition and glycosyl linkages indicated the presence of pectic polysaccharides in the CDTA fractions. The structure of such pectic polysaccharides was investigated by enzymatic digestion and spectral studies. The CDTA fractions of leaf and stem cell-wall preparations were treated with polygalacturonanase to digest the pectins. The mass spectral analysis of the enzymatic digests indicated the presence of oligogalaturonides in 4-15 degrees of polymerization (DP) containing varied degrees of methyl groups. These oligogalaturonides could be derived from homogalacturonans (HGAs), which consisted of the methyl ester of GalA. The pectins isolated from *Angelica auctiloba* and *plantogo major* were shown to have anti-complement effect. The plants Noni (*Morinda citrifolia*) and *Panax notoginseng*, which contain high level of HGA, have medicinal applications. Thus, the high content of HGA in the pectin components of *D. huoshanense* contributes to its bioactivity.

In agreement with the structural deduction, the $^1$H NMR spectrum (600 MHz) of the polysaccharides in CDTA fractions showed an intense singlet at δ 3.7 for the methyl ester (CO$_2$CH$_3$) and a broad multiplet at δ 4.3 attributable to the C-4 protons in GalA or its methyl ester. In the $^{13}$C NMR spectrum, the signals for the methyl ester appeared at δ 52.7 (CH$_3$) and 170.6 (C=O), whereas the corresponding carboxyl signal of GalA occurred at δ 172.6. The $^1$H NMR spectrum of the pectic polysaccharides also showed a weak signal of doublet at δ 1.29 that might be ascribed as the methyl group in rhamnose, of which presence was shown by composition and glycosyl linkage analyses (Tables 3 and 4).

Analysis of the Heteroxylans in 1 M KOH Fraction

The 1 M KOH fraction of leaf cell-wall preparation was hydrolyzed with the enzyme endo-(1→4)-β-D-xylanase, and the released oligosaccharides were analyzed by mass spectrometry. The characteristic signals at m/z 877, 1009, 1141 and 1273 correlated with the [M+Na]$^+$ ions of Pen$_5$GlcA, Pen$_6$GlcA, Pen$_7$GlcA, and Pen$_8$GlcA, (where Pen represents pentoside) whereas the signals at m/z 1023 and 1155 were attributed to the [M+Na]$^+$ ions of Pen$_6$MeGlcA and Pen$_7$MeGlcA. These results were consistent with the high contents of GlcA and MeGlcA observed in the uronic acid analysis (Table 3). Similarly, enzymatic digestion and MS analysis of the 1 M KOH fraction of stem cell-wall preparation found the presence of the pentose oligomers of Pen$_x$GlcA (x=5-9), Pen$_y$MeGlcA (y=4-9) and Pen$_z$(MeGlcA)$_2$ (z=5-11). The pentose oligomers with substitution of (MeGlcA)$_2$ disaccharide were found in stems only, but not found in leaves.

L-Arabinose is observed at the terminal of the oligosaccharides by treatment with α-L-arabinosidase. After the enzymatic removal of arabinosyl residues, the overall mass profile for the GlcA- and MeGlcA-substituted pentose-oligomers did not change, albeit all the [M+Na]$^+$ ions showed a reduction of 132 daltons in comparison with the original mass signals for the sample without α-L-arabinosidase treatment. This experiment clearly indicated the presence of mono-substitute arabinosyl residue at the terminal, a characteristic of glucuronoarabinoxylans (GAXs).

Analysis of the Xyloglucans in 4 M KOH Fraction

The 4 M KOH fraction of leaf cell-wall preparation was subjected to enzymatic degradation by endo-(1→4)-β-D-glucanase. The hydrolysate was analyzed by high pH anion exchange chromatography-pulsed amperometric detection (HPAEC-PAD) and MALDI-TOF MS, shown in FIG. 8 to show the presence of xyloglucans (XGs). The [M+Na]$^+$ ions in the MS spectrum corresponded to XXG (m/z 791), XXGG (m/z 953), XXXG (m/z 1085), XLXG/XXLG (m/z 1247), XXFG (m/z 1393), XLLG (m/z 1409), and XLFG (m/z 1555), where G represents the backbone Glc in β1,4-linkage, X represents the Xyl(α1,6)Glc unit, L represents Gal(β1,2)Xyl(α1,6)Glc, and F represents Fuc(α1,2)Gal(β1,2)Xyl(α1,6)Glc. The similar composition of XGs was found in the stem cell-wall preparation of *D. huoshanense*. Results showed that the XGs of *D. huoshanense* have both XXGG and XXXG backbones with fucosylated XG oligosaccharides XXFG and XLFG. XGs with terminal Fuc and Gal side-chain have been shown to induce anti-tumor activity in cell-base assays.

Analysis of the Polysaccharides in Stem Mucilage

The presence of glucomannan was confirmed by using glucomannan assay kit. The de-starched mucilage polysaccharide hydrolysate was found to contain Man (79%) and Glc (21%) as deduced from the corresponding alditol acetates in the GC-MS analyses. Accordingly, the mass spectrum of endo-(1→4)-β-D-mannanase hydrolysate of the mucilage polysaccharide gave the molecular ions attributable to glucomanno-oligosaccharides of 3-9 degrees of polymerization (DP) with partial acetylation.

Figure 10:
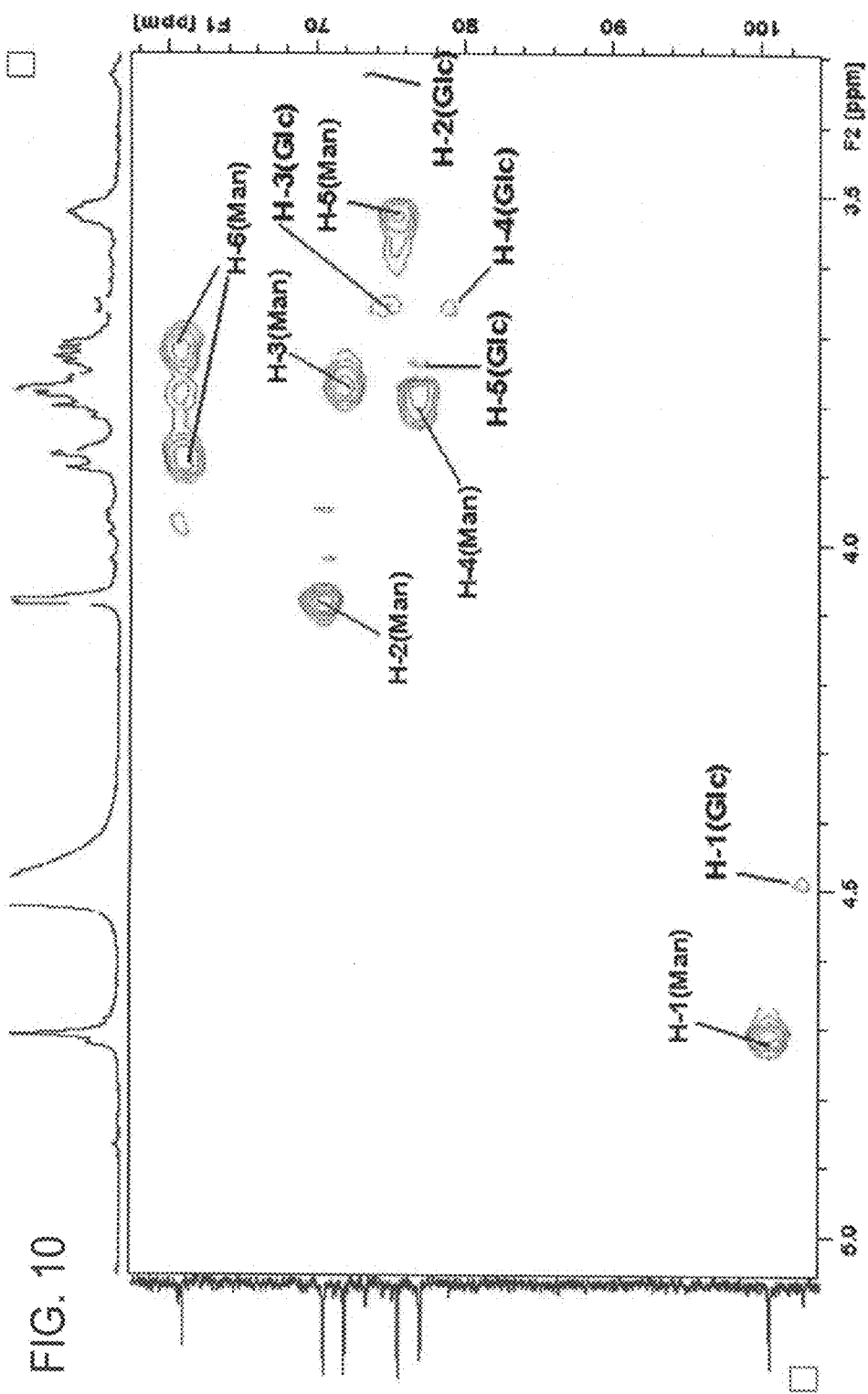
FIG. 10 is a graph showing implementations of illustrative data of an HSQC spectrum of the deacetylation product from the glucomannan of stem mucilage.

In agreement with the structural assignments of β-(1→4)-D-Glc*p* and β-(1→4)-D-Man*p*, their anomeric carbons appeared at δ 102.8 (minor component) and 100.6 (major component), respectively. The degree of acetylated mannose was estimated to be 25%. In addition to the signals at δ$_H$ 2.20/δ$_C$ 20.3 and δ$_C$ 173.5 for the acetyl group of 2-O-acetyl-β-(1→4)-D-mannose, the minor signals (~5%) occurring at δ$_H$ 2.05/δ$_C$ 20.5 and δ$_C$ 174.0 might be attributable to 3-O-acetyl-β-(1→4)-D-mannose. Moreover, the mucilage polysaccharide was treated with 3 M NaOH (or 1 M NaOH+ 1% NaBH$_4$) to remove acetyl groups. After dialysis, the deacetylated polysaccharide showed the $^1$H—$^{13}$C signals in the heteronuclear single quantum coherence (HSQC) spectrum were assigned according to literature. The HSQC spectrum clearly indicated that the deacetylated mucilage polysaccharide was composed of (β1→4)-linked D-Man*p* and (β1→4)-linked D-Glc*p*, as shown in FIG. 10.

Bioactivities of the Polysaccharides and the Deacetylated Polysaccharides from Mucilage Preparations The MTS assay was used to determine the cell proliferation effects of the polysaccharide fractions from the different *D. huoshanense* structures. As shown in Table 5 mice splenocytes incubated with mucilage fractions significantly grew faster than untreated cells (154% for stem mucilage and 141% for leaf mucilage vs. 100% for control cells).

TABLE 5

Cell proliferation and cytokines induced by different polysaccharide fractions from *D. huoshanense*.

| | Cell Prolif. | Cytokine Quantitation (pg/mL)[b] | | | | | |
|---|---|---|---|---|---|---|---|
| | (%)[a] | GM-CSF | G-CSF | IFN-γ | IL-10 | IL-1α | IL-6 |
| Untreated cells | 100 | <50 | <50 | <50 | <50 | <50 | <50 |
| ConA | 155 ± 5 | 408 ± 58 | 46 ± 9 | 1504 ± 387 | 590 ± 75 | 79 ± 42 | 511 ± 20 |
| Glucomannan[c] | 106 ± 2 | NA[e] | NA[e] | <50 | <50 | 117 ± 8 | <50 |
| Mannan[d] | 106 ± 2 | NA[e] | NA[e] | <50 | <50 | 92 ± 8 | <50 |
| Leave mucilage | 141 ± 2 | 95 ± 17 | 582 ± 56 | 1563 ± 424 | 241 ± 9 | 322 ± 48 | 451 ± 23 |
| Stem mucilage | 154 ± 4 | 118 ± 18 | 660 ± 58 | 1465 ± 447 | 286 ± 30 | 260 ± 91 | 476 ± 17 |
| Deacetyl-mucilage | 100 ± 1 | <50 | <50 | <50 | <50 | <50 | <50 |

[a]Mice splenocytes (5 × 10$^5$) were incubated with 50 μg/mL of different polysaccharide fractions for 60 h, and then subjected to MTS assay as described in Materials and Methods. The OD at 492 nm of individual samples was normalized against the OD$_{492}$ of the untreated cells, which were defined as 100% cell proliferation.
[b]After cells were incubated with 50 μg/mL of indicated preparations for 48 h, the culture medium was harvested and the cytokine production was analyzed using Quantikine mouse ELISA kits.
[c]Glucomannan from konjac.
[d]Mannan from ivory nut.
[e]Not available.

Figure 11:
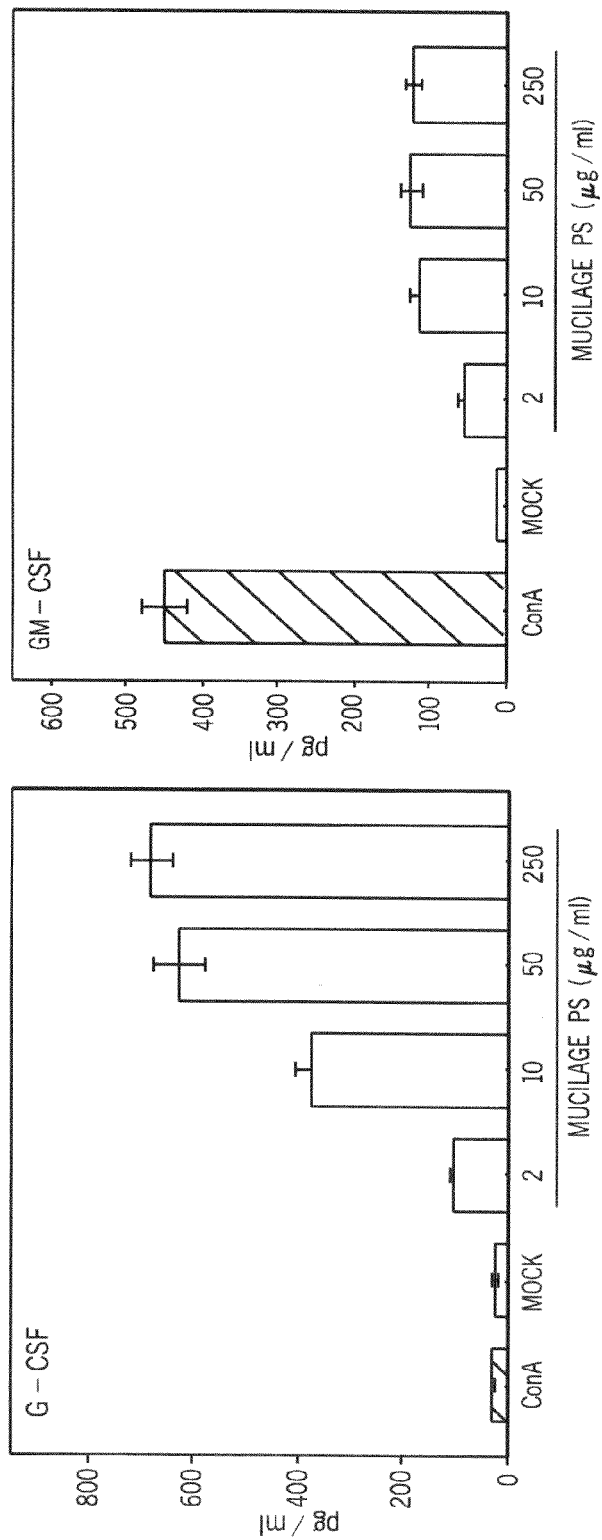
FIG. 11 are graphs of implementations of illustrative data of the dose-response relationship of mucilage polysaccharide on the production of cytokines and hematopoietic growth factors.

The effects are more obvious compared with the glucomannan from konjac and the mannan from ivory nut. The cytokine profiling indicated an increased expression of several cytokines including IFN-γ, IL-10, IL-6, and IL-1α. Significant amounts of hematopoietic growth factors GM-CSF and G-CSF were also induced. The dose-dependent effects of the stem mucilage polysaccharide on the G-CSF and GM-CSF induction was examined. The stimulatory effects on the production of both factors were dose-dependent, up to 250 μg/mL, as shown in FIG. 11.

Most interestingly, the inventors investigated whether structural modification of stem mucilage polysaccharide by deacetylation of 2-O-acetyglucomannan would affect its stimulatory effect on cytokine production. Treatment of cells with the deacetylated stem mucilage polysaccharide was found to maintain cell proliferation, but failed to induce cytokine production (see Table 5).

Figure 12:
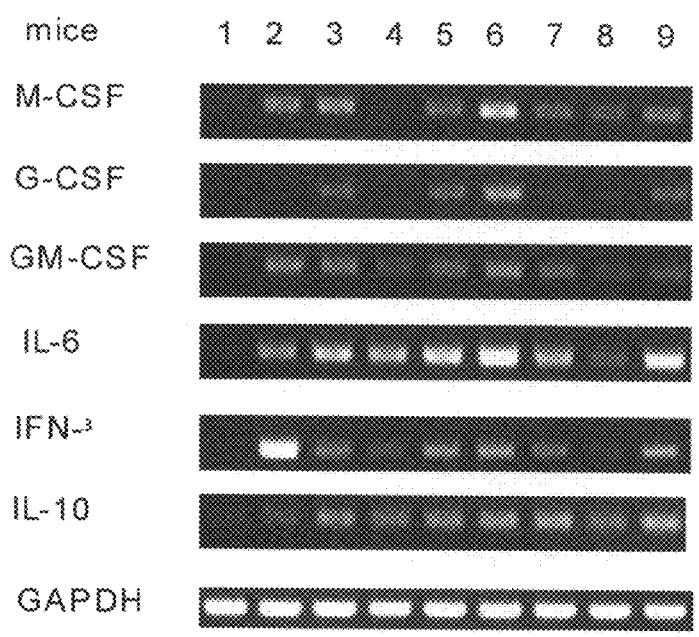
FIG. 12 is a graph of illustrative data of assessment of cytokines (G-CSF, IL-10, IFN-γ, IL-6, GM-CSF, and M-CSF) by RT-PCR on treatment of mouse splenocytes with different drugs for 12 hours.

Validation of Structure and Bioactivity Via Fractionation of Mucilage Components The extract of mucilage was fractionated by anion-exchange chromatography on DEAE-cellulose ($NH_2$— form). Elution with distilled water afforded neutral polysaccharides, and the subsequent elution with aqueous NaCl buffer gave the uronic acid and aldonic acid containing polysaccharides. Six fractions were obtained, and each fraction was subjected to dialysis (molecular-weight cutoff=500) to remove salt. The most potent fraction (6% of weight) in cytokines expression was further separated by size-exclusion chromatography on Sephacryl S-200 into fractions A (31%), B (13%), C (18%), D (17%), E (8%), and F (13%). The cytokines expression of these polysaccharide fractions were inferred from the RT-PCR analyses, as shown in FIG. 12. Though G-CSF was not induced by Con A (lane 2), the cytokine expression on treatment with the polysaccharides from mucilage (lane 3) and fractions B-F (lanes 5-9) were confirmed.

The composition and structure for the polysaccharide of fraction B were rigorously determined by a combination of chemical, enzymatic, and spectroscopic methods. The polysaccharide of fraction B was subjected to hydrolysis with trifluoroacetic acid to release the monosaccharide components, which were subsequently reduced by $NaBH_4$ and acetylated by $Ac_2O$ to give the corresponding alditol peracetates. The GC-MS analysis of such alditol peracetates correlated to the polysaccharide of fraction B with the composition of mannose and glucose in a ratio of 10:1. On the other hand, the polysaccharide of fraction B was subjected to methylation, acid-catalyzed hydrolysis, reduction, and acetylation to give the corresponding methylated alditol peracetates, which was determined by GC-MS analysis to reveal the glycosyl linkages. By this method, the polysaccharide of fraction B was deduced to have a backbone consisting of (1→4)-linked Manp and Glcp.

Figure 13:
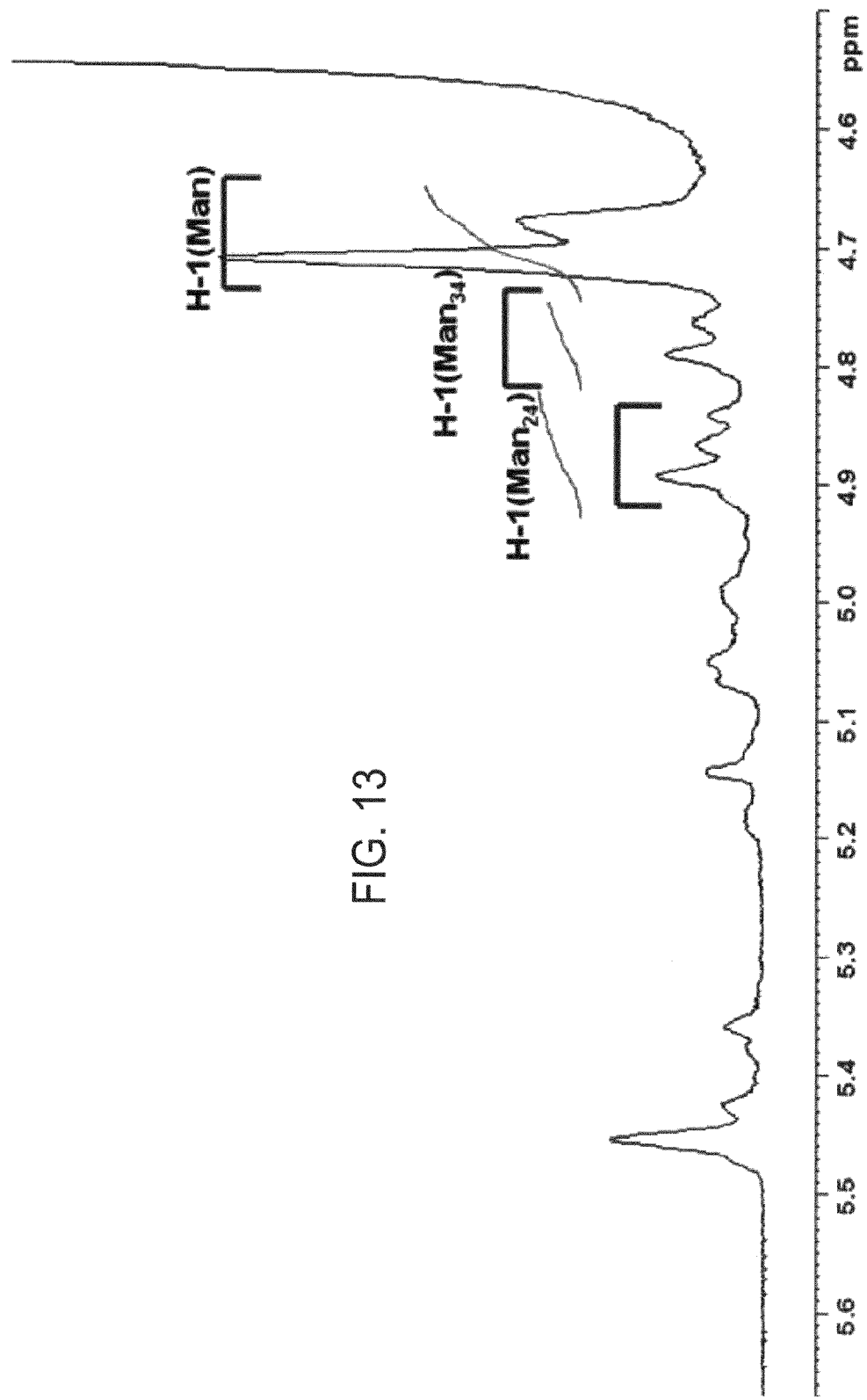
FIG. 13 is a graph of illustrative data of an $^1$H NMR spectrum of the polysaccharide of fraction B in $D_2O$ shows the ratio of Manp/2-O-AcManp/3-O-AcManp=66:19:15.

The degree of acetylation in the polysaccharide of fraction B was determined by the NMR analysis, as shown in FIG. 13. The NMR spectrum showed the characteristic anomeric protons (H-1) for unacetylated mannopyranoside (Man), 2-O-AcManp ($Man_{24}$), and 3-O-AcManp ($Man_{34}$) at δ 4.64-4.74, 4.93-4.82, and 4.74-4.81, respectively, in a ratio of 66:19:15 deduced from the integration of individual Manp signals in the polysaccharide of fraction B.

Figure 14A:
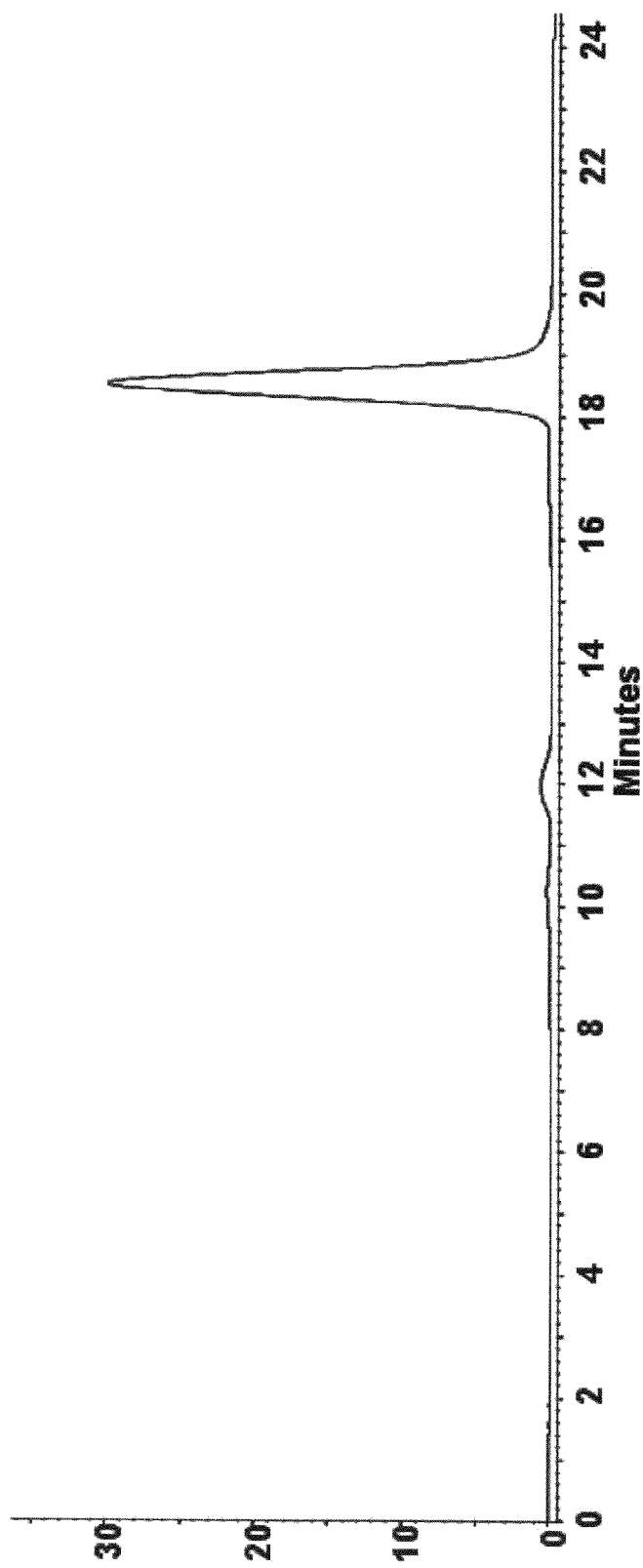
FIG. 14 is a graph of illustrative data of a refractive-index profile of HPSEC analysis of the polysaccharides in fraction B on the SEC-1000 column (panel a) and G-3000 column (panel b)
Figure 14B:
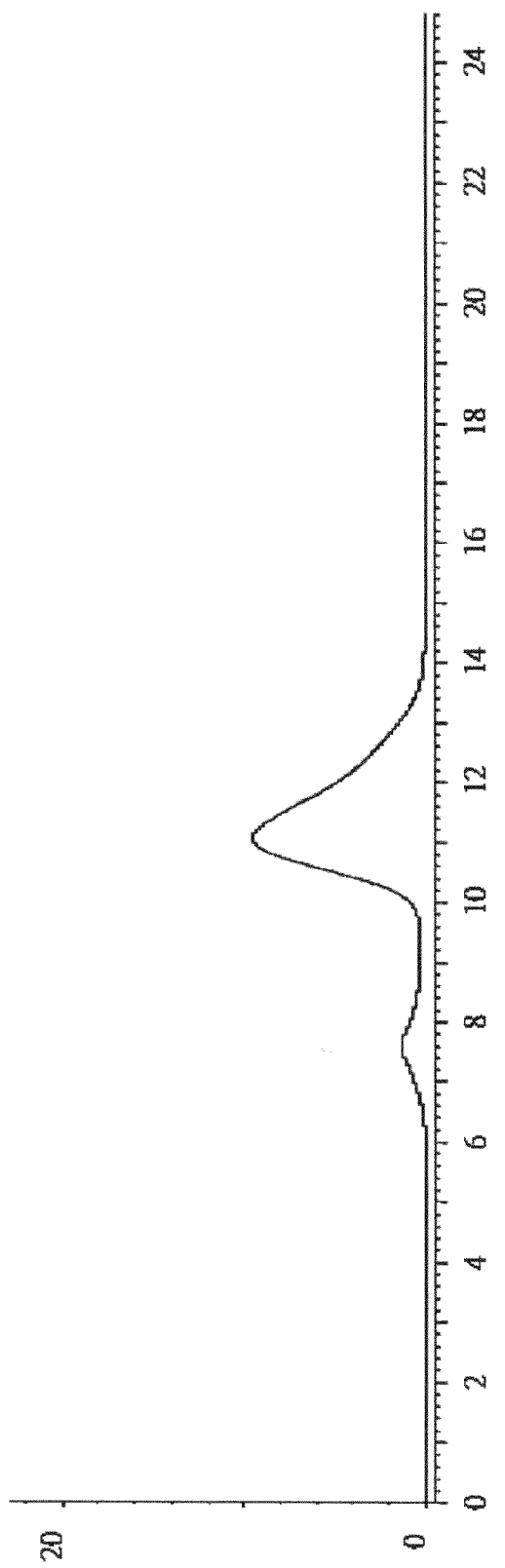

High performance size exclusion chromatography (HPSEC) coupled with RI and UV detection was used to estimate the homogeneity and molecular weight of the polysaccharide in fraction B. The retention times on two different HPLC columns (Thermo BioBasic SEC-1000 and TSK-GEL G3000 columns) were measured as shown in FIG. 14, and the molecular weight of the dominant component was estimated to be ~10 KDa by calibration with pullulan standards.

In an alternative approach, diffusion-ordered NMR spectroscopy (DOSY) experiment was used to evaluate the molecular weight of polysaccharide based on equation 1, where D is the diffusion coefficient and MW is the molecular weight of the examined polysaccharide.

$$D = 8.2 \times 10^{-9} MW^{-0.50} (m^2 s^{-1}) \quad (1)$$

Figure 15:
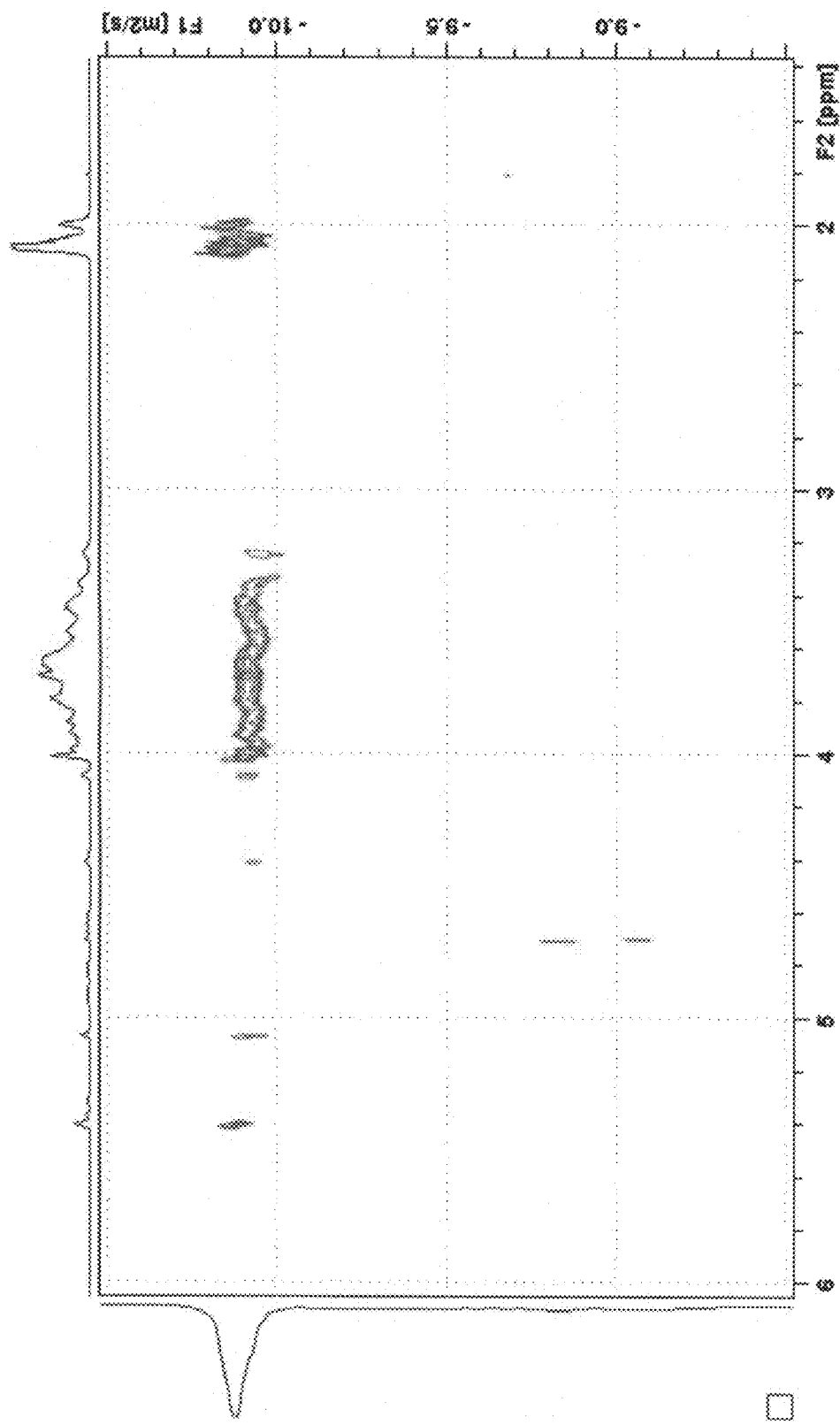
FIG. 15 is a graph of illustrative data of a DOSY spectroscopy of fraction B. The molecular weight of 9.7 KDa was deduced from the equation $D=8.2\times10^{-9}$ $MW^{-0.50}$ ($m^2$ $s^{-1}$) with the diffusion coefficient of −10.08.

The measured D value of −10.08 corresponded to an average molecular weight of 9.7 KDa as shown in FIG. 15, in agreement with that deduced from the HPSEC analysis. Thus, fraction B was attributable to a glucomannan polysaccharide of ~60 DP with partial acetylation.

Figure 16:
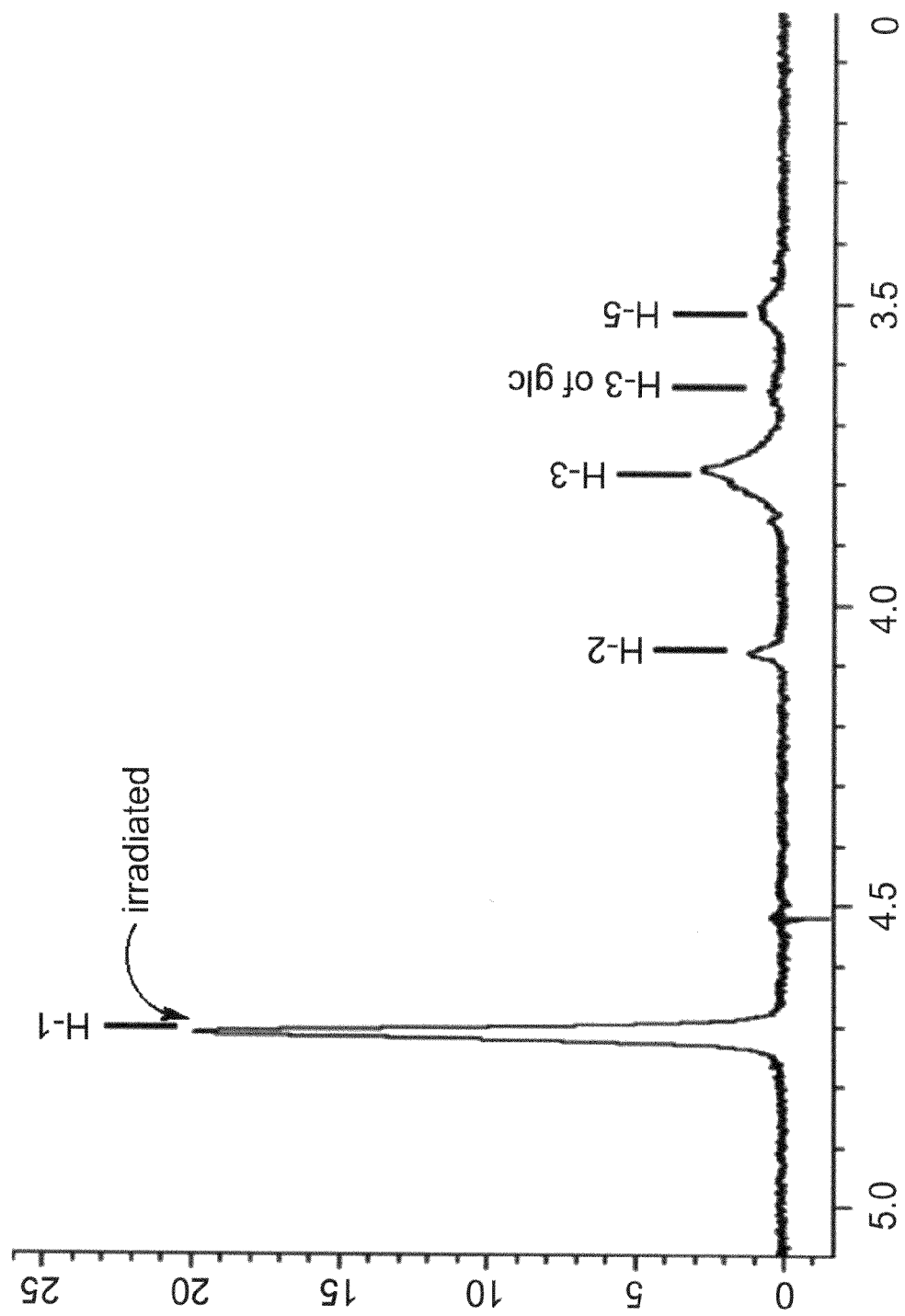
FIG. 16 is a graph of illustrative data of the differential NOE spectrum of fraction B showing the mannoside units in the β-glycosidic linkage.

Nuclear Overhauser Enhancement (NOE), which depends on the interplay of proximal protons, provides valuable information for assessment of molecular conformation and proton assignment. In general, intramolecular NOE signals were observed in the proton pair having disposition of 1,3-diaxial or vicinal equatorial-axial relationship in a pyranosyl ring. Thus, the anomeric proton (H-1) in β-D-mannoside would exert NOEs to H-2, H-3 and H-5, whereas α-D-mannoside would show only a strong NOE between H-1 and H-2. Accordingly, the polysaccharide of fraction B was determined to contain the mannosides with β-linked configuration. Thus, the H-1 resonance of unacetylated mannopyranosyl residues, which were linked to either mannopyransyl or glucopyranosyl residues, was selected for irradiation to give the differential NOE spectrum (FIG. 16). The intra-residue NOEs with the H-2, H-3, and H-5 in mannopyranoside and the inter-residue NOE with the H-3 in glucopyranoside were observed. This result was in agreement with the β-linked configuration of mannosides in the glucomannan.

The acetyl groups in the polysaccharide of fraction B were removed by treatment with 3 M NaOH. The de-esterified glucomannan was then subjected to enzymatic digestion to determine the glycosidic linkages. After digestion with endo-β-mannase or β-mannosidase, the hydrolysate was found to contain significant amounts of mannose and oligomannosides in a series, by comparison with the standards on HPAEC-PAD analyses. In contrast, no free mannose was released by treatment of the decetylated glucomannan with α-mannosidase. These enzyme assays thus confirmed the β-linkage of mannosides in the polysaccharide of fraction B.

The 2D-NMR spectra further provided information for the structural assignment. Due to the deshielding effect of acetyl group, three sets of H-2 in 2-O-acetylated β-Manp units occurred at δ 5.45, 5.42, and 5.36, whereas two sets of H-2 in 3-O-acetylated β-Manp units appeared at δ 5.05 and 4.99. Correlations of the protons with carbon signals were found by correlation spectroscopy (COSY), total correlation spectroscopy (TOCSY), HSQC, heteronuclear multiple bond correlation (HMBC), and rotating-frame Overhauser effect spectra (REOSY). The anomeric proton and carbon at the reducing end of α-Manp residue was readily identified at $δ_H$ 5.14 and $δ_C$ 94.4 in the HSQC spectrum of fraction B. The (1→4)-linked β-Glc residue was characterized by the cross-peak between $δ_H$ 4.48 and $δ_C$ 102.8 in the HSQC spectrum.

Figure 17A:
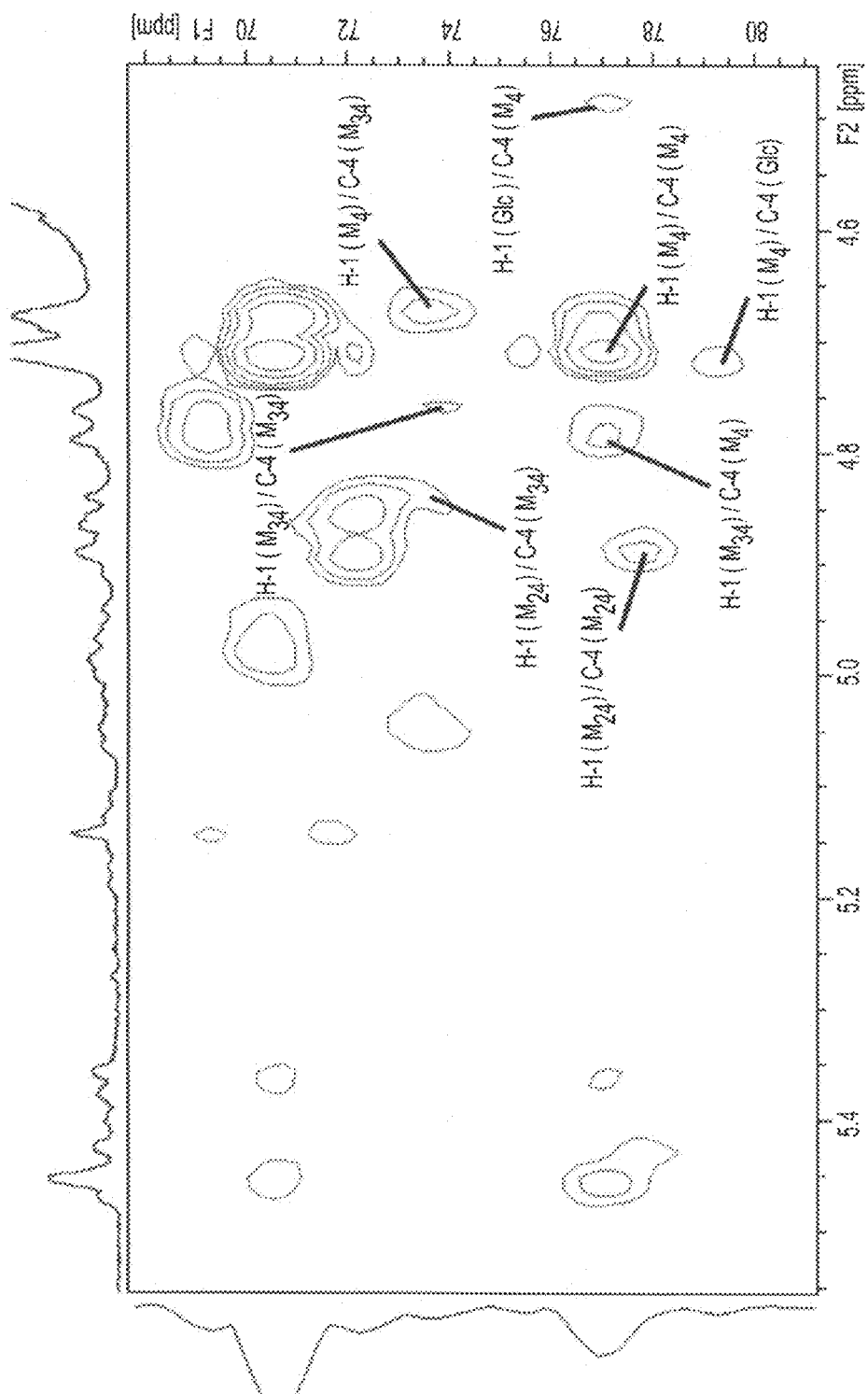
FIG. 17 are graphs of implementations of illustrative data of HMBC spectrum of fraction B.
Figure 17B:
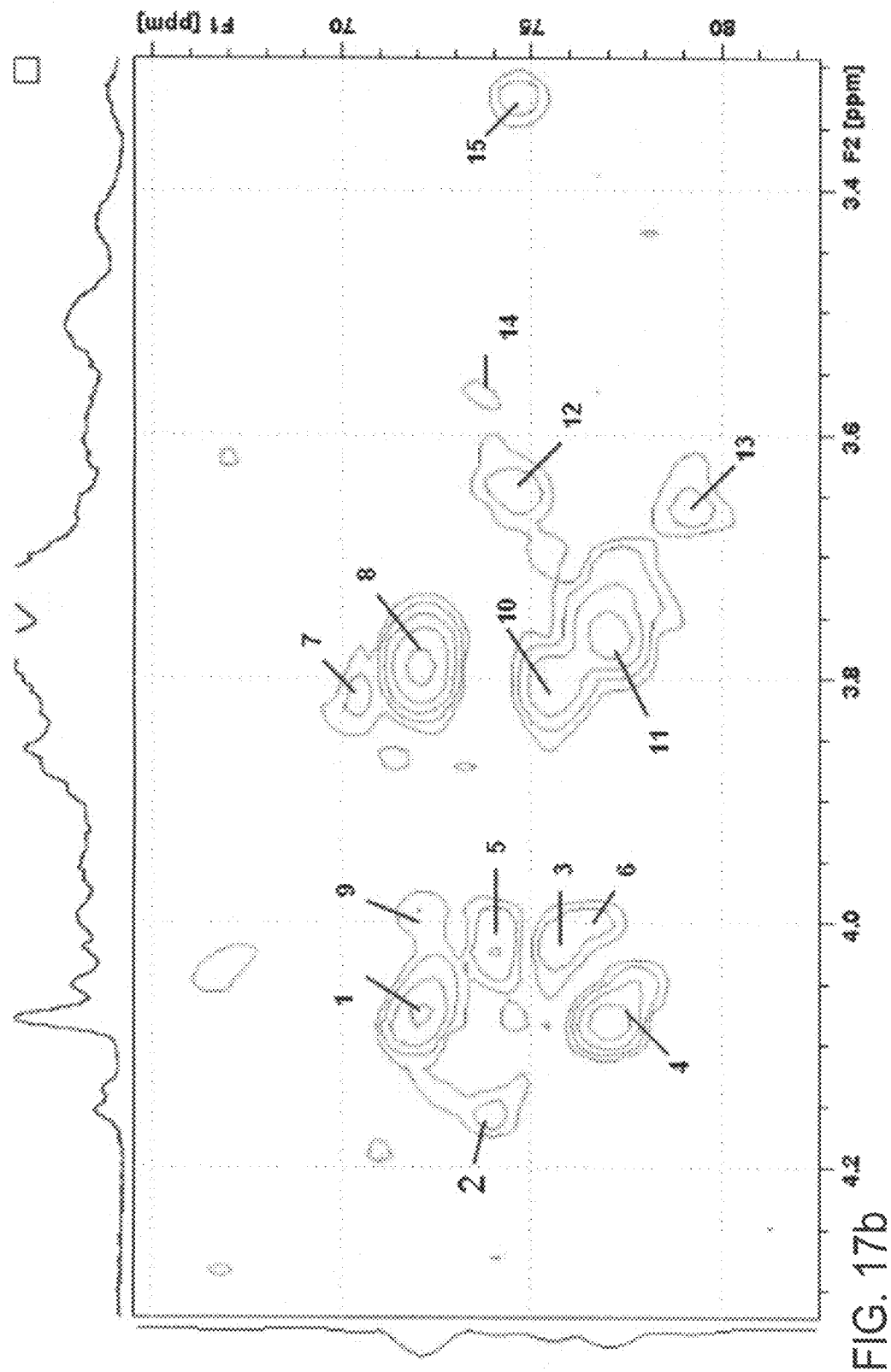

In addition to the intra-glycosidic correlations of proton and carbon signals, the HMBC spectrum, as shown in FIG. 17, revealed the inter-residue cross-peaks of the anomeric proton (H-1) with the C-4 of the adjacent saccharide unit via the $^3$J-coupling. Thus, the HMBC spectrum manifested the existence of the disaccharide units ManGlc, ManMan, Man-$Man_{34}$, $Man_{24}Man_{24}$, $Man_{24}Man_{34}$, $Man_{34}Man$, and Glc-Man.

Figure 18:
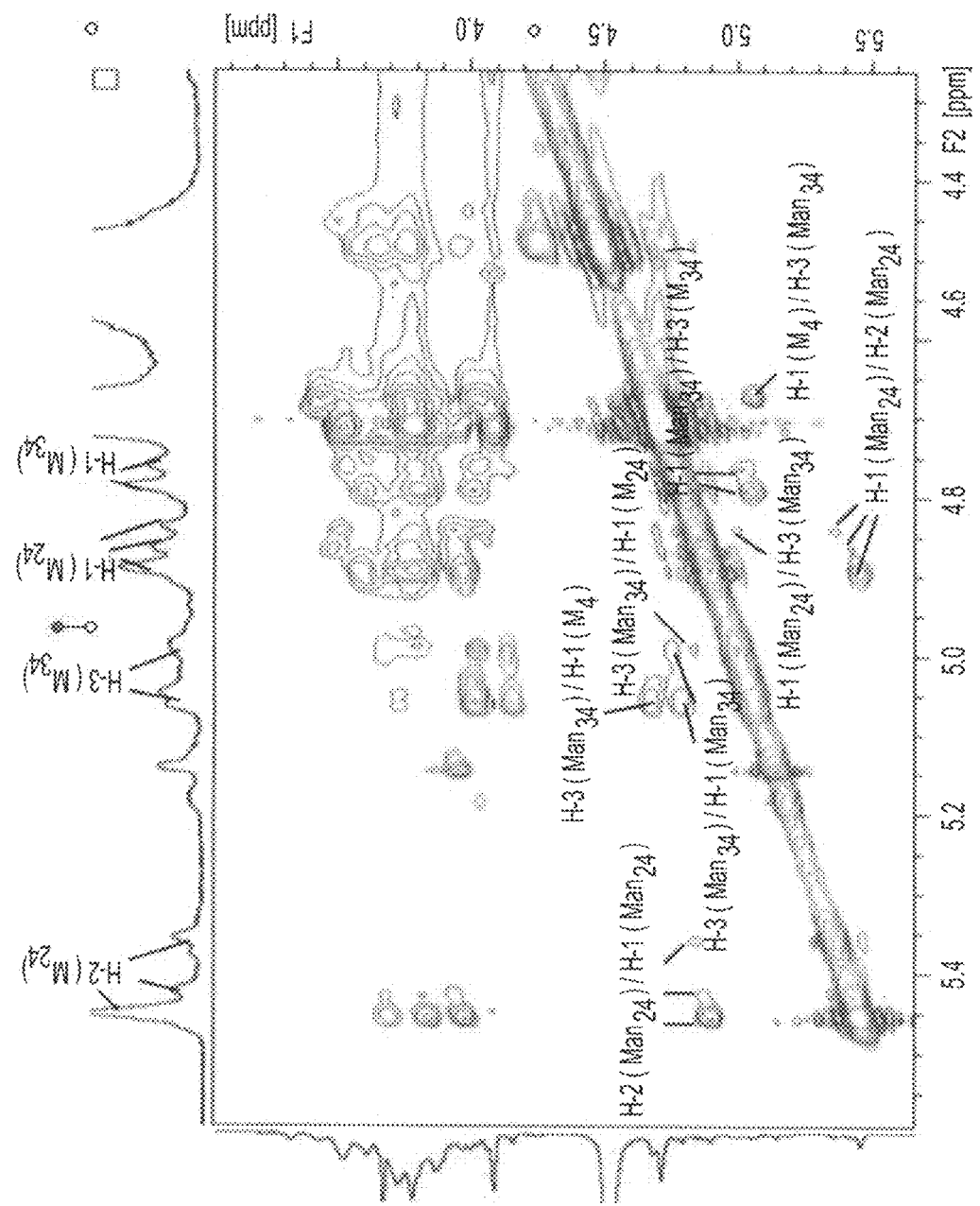
FIG. 18 is a graph of illustrative data of a ROESY spectrum of fraction B shows the intra- and inter-glycosidic correlations (indicated by quotation marks) in the glucomannan.

In the ROESY spectrum, as shown in FIG. 18, the anomeric proton (H-1) of acetylated β-Manp displayed three intra-residue cross-peaks, namely H-1/H-2, H-1/H-3, and H-1/H-5 due to their short spatial distances similar to those found in the NOE spectrum, as shown in FIG. 15. In addition, the sequential inter-residue correlations, such as "H-1(Man)/H-3($Man_{34}$)" (δ 4.68/5.05) and "H-1($Man_{24}$)/H-3($Man_{34}$)" (δ 4.84/4.99), also indicated a great population of the fragments $ManMan_{34}$ and $Man_{24}Man_{34}$.

On the basis of the aforementioned 1D- and 2D-NMR spectral studies and by analogy to the previous relevant reports, the $^1$H and $^{13}$C NMR spectral data of the polysaccharide in fraction B are summarized in Table 6.

TABLE 6

$^1$H and $^{13}$C NMR chemical shifts (in δ values) for the polysaccharide in fraction B.

| Sugar residues | Linkage | | 1 | 2 | 3 | 4 | 5 | 6 |
|---|---|---|---|---|---|---|---|---|
| →4)-β-D-Glc-(1→ | GlcMan | $\delta_H$ | 4.48 | 3.32 | 3.66 | 3.65 | 3.50 | 3.79, 3.66 |
| | | $\delta_C$ | 102.8 | 73.5 | 74.6 | 79.2 | 74.8 | 60.6 |
| →4)-β-D-Man-(1→ | ManGlc, ManMan | $\delta_H$ | 4.71 | 4.08 | 3.77 | 3.79 | 3.52 | 3.86, 3.72 |
| | | $\delta_C$ | 100.6 | 70.5 | 71.9 | 77.2 | 75.5 | 61.1 |
| →4)-β-D-Man-(1→ | ManMan$_{34}$ | $\delta_H$ | 4.68 | 4.05 | 3.76 | 3.75 | 3.44 | nd |
| | | $\delta_C$ | 100.6 | 70.6 | nd | 77.7 | 75.3 | nd |
| →4)-2-O-acetyl-β-D-Man-(1→ | Man$_{24}$Man | $\delta_H$ | 4.89 | 5.45 | 3.99 | 3.83 | 3.58 | 3.91 |
| | | $\delta_C$ | 99.6 | 72.1 | 70.6 | 77.3 | 76.4 | 60.4 |
| →4)-2-O-acetyl-β-D-Man-(1→ | Man$_{24}$Man$_{24}$ | $\delta_H$ | 4.87 | 5.42 | 3.95 | 3.82 | 3.48 | 3.96, 3.79 |
| | | $\delta_C$ | 99.4 | 72.1 | 70.7 | 77.9 | 76.3 | nd |
| →4)-2-O-acetyl-β-D-Man-(1→ | Man$_{24}$Man$_{34}$ | $\delta_H$ | 4.84 | 5.36 | 3.93 | 3.82 | 3.50 | nd |
| | | $\delta_C$ | 99.2 | 72.0 | 70.6 | 77.2 | 76.3 | nd |
| →4)-3-O-acetyl-β-D-Man-(1→ | Man$_{34}$Man | $\delta_H$ | 4.79 | 4.15 | 5.05 | 4.00 | 3.60 | nd |
| | | $\delta_C$ | 100.0 | 69.2 | 74.0 | 73.7 | 75.7 | nd |
| →4)-3-O-acetyl-β-D-Man-(1→ | Man$_{34}$Man$_{24}$ | $\delta_H$ | 4.76 | 4.14 | 4.99 | 4.03 | 3.55 | nd |
| | | $\delta_C$ | 100.2 | 69.2 | 74.4 | 73.7 | 75.7 | nd | nd = not determined.

Figure 19:
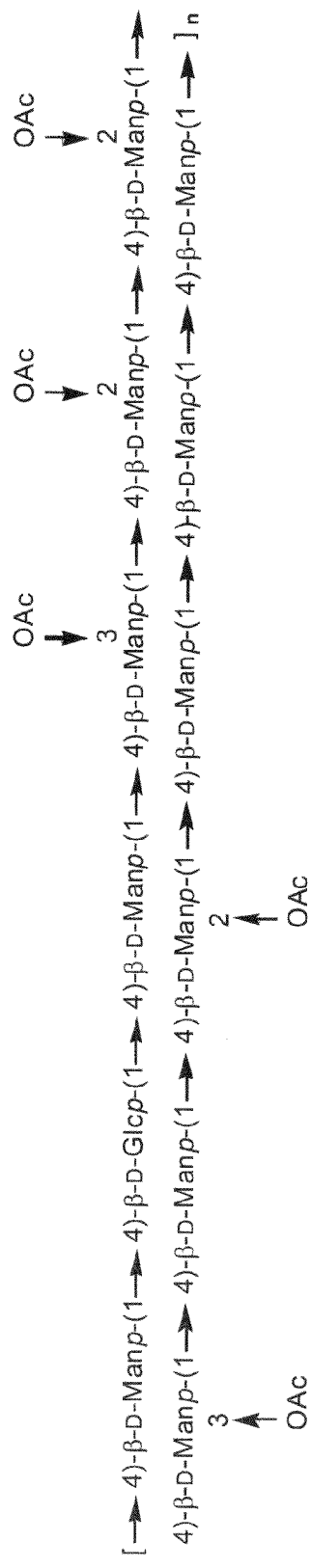
FIG. 19 is a graph of illustrative data of a tentative partial structure of the polysaccharide in fraction B.
Figure 20:
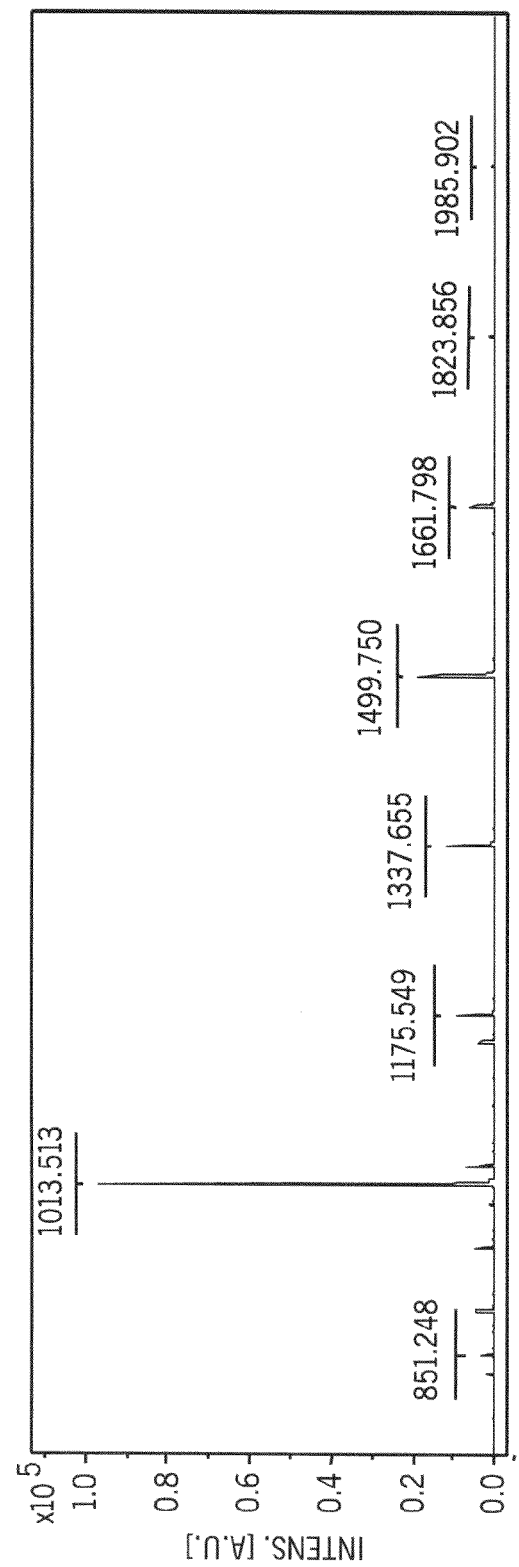
FIG. 20 is a graph of an implementation of a mass spectrum of an oligomannose containing 66% $(Man)_6$+34% $(Man)_n$ (n≧7)

A partial structure for the acetyl-glucomannan is tentatively depicted in FIG. 19 to account for the ratio of glucoside to mannoside (~1:10) and the degree of acetylation (~35%).

DHPS Induces Expression of G-CSF

Figure 4:
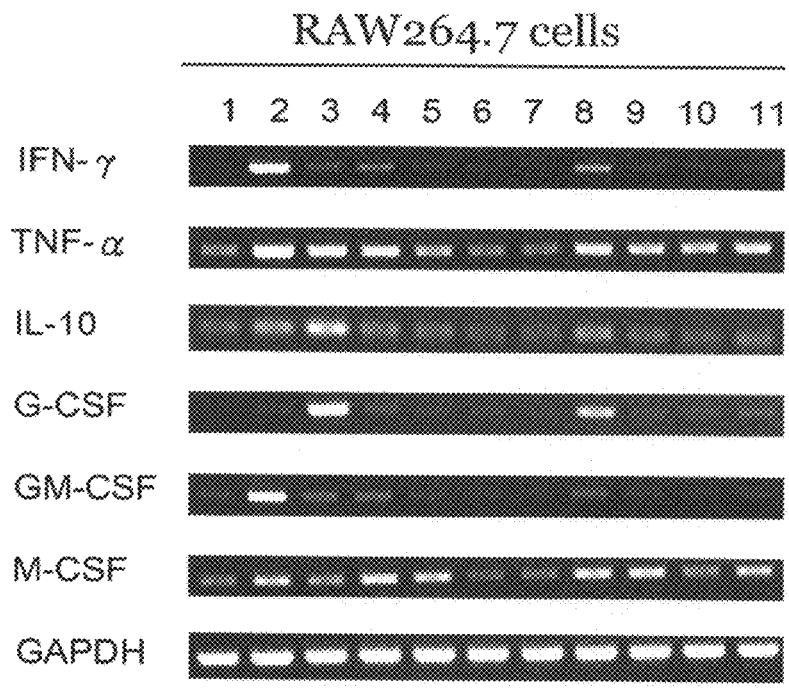
FIG. 4 is a graph of implementations of experimental data assessing cytokines (IFN-γ, TNF-α, IL-10, G-CSF, GM-CSF, and M-CSF) by RT-PCR on cultured mice macrophage RAW264.7 cells with different samples for 12 hours.
Figure 5:
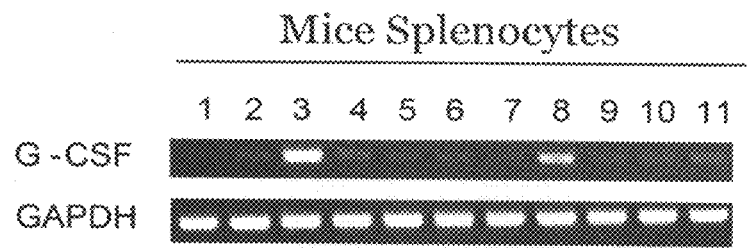
FIG. 5 is a graph of implementations of experimental data assessing G-CSF by RT-PCR on mice splenocytes with different samples for 12 hours.

As shown in FIGS. 4 and 5, the RT-PCR assays indicate that the crude extract of *D. huoshanense* polysaccharide (DHPS, lane 3) and a 1,4-β-D-oligomannose mixture (M003) containing 66% (Man)$_6$+34% (Man)$_n$ (n≧7, lane 8) can induce expression of G-CSF, whereas the mannose or galactosylmannose oligomers in low degrees of polymerization (x≦5) are relatively inactive (lanes 4-7 and 9-11). In FIGS. 6 and 7, ELISA assays confirm that the oligomannose mixture M003 can induce expression of G-CSF in time- and dose-dependent manner with somewhat higher activity than DHPS. A comparison experiment (FIG. 8) further supports the high activity of DHPS and the oligomannose mixture M003 (DP≧6). Another oligomannose M013 (DP=5-10) obtained by enzymatic (hemicellulase) degradation of high-molecular-weight mannan is the most potent ingredient to induce expression of G-CSF.

The glucomannan isolated from the mucilage of *D. huoshanense* with β-(1→4) linkages and partial acetylation is found to induce the expression of G-CSF, IL-6, or other cytokines as disclosed herein. However, the deacetylated mucilage obtained from an alkaline treatment fails to induce cytokine production. Losses of activity are also found in the saponification products of DH007, DH023, Man020 and Man021 in comparison with their acetylated precursors DH006, DH020, M013 and Man018, respectively. On the other hand, the study also indicates that excessive acetylation of the oligomannose mixture M003 may decrease the activity in inducing expression of G-CSF (comparing entry 3 with entries 4-9 in Table 2). It is presumed that oligomannoses with DP≧6 are real activator to induce expression of cytokines. For high-molecular weight of (gluco)mannan in *D. huoshanense* (e.g., ~60 DP, disclosed herein), proper degree of acetylation may improve solubility and absorption in physiological conditions to facilitate induction of cytokines.

Pharmaceutical or Nutraceutical Compositions

According to another aspect, the polysaccharides or fractions of *D. huoshanense* can be included in a pharmaceutical or nutraceutical composition together with additional active agents, carriers, vehicles, excipients, or auxiliary agents identifiable by a person skilled in the art upon reading of the present disclosure.

The pharmaceutical or nutraceutical compositions preferably comprise at least one pharmaceutically acceptable carrier. In such pharmaceutical compositions, the polysaccharides or fractions of *D. huoshanense* forms the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Subject as used herein refers to humans and non-human primates (e.g., guerilla, macaque, marmoset), livestock animals (e.g., sheep, cow, horse, donkey, and pig), companion animals (e.g., dog, cat), laboratory test animals (e.g., mouse, rabbit, rat, guinea pig, hamster), captive wild animals (e.g., fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

According to implementations, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811, which is incorporated by reference herein.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds may be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected location to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the active compound (i.e., an effective dosage) may range from about 0.001 to 100 g/kg body weight, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

According to another aspect, one or more kits of parts can be envisioned by the person skilled in the art, the kits of parts to perform at least one of the methods herein disclosed, the kit of parts comprising two or more compositions, the compositions comprising alone or in combination an effective amount of polysaccharides or fractions of *D. huoshanense* according to the at least one of the above mentioned methods.

The kits possibly include also compositions comprising active agents other than the polysaccharides or fractions of *D. huoshanense*, identifiers of a biological event, or other compounds identifiable by a person skilled upon reading of the present disclosure. The term "identifier" refers to a molecule, metabolite or other compound, such as antibodies, DNA or RNA oligonucleotides, able to discover or determine the existence, presence, or fact of or otherwise detect a biological event under procedures identifiable by a person skilled in the art; exemplary identifiers are antibodies, exemplary procedures are western blot, nitrite assay and RT-PCR, or other procedures as described in the Examples. Exemplary biological events are cytokine expression or other immunomodulating events; an exemplary active agent other than polysaccharides or fractions of *D. huoshanense* is LPS.

The kit can also comprise at least one composition comprising an effective amount of polysaccharides or fractions of *D. huoshanense* or a cell line. The compositions and the cell line of the kits of parts to be used to perform at least one method herein disclosed according to procedure identifiable by a person skilled in the art.

According to implementations, the polysaccharides or fractions of *D. huoshanense* may be used in an herbal, food, or dietary supplements (including vitamins and other related formulations) to induce the secretion of proteins, such as cytokines or growth factors, for example. Such supplements are prepared with carriers as outlined above and administered as described above. According to implementations, the polysaccharides or fractions of *D. huoshanense* induce or upregulate beneficial proteins, or depress or downregulate undesirable proteins, as understood by artisans.

EXAMPLES

Example 1

Materials

*Dendrobium huoshanense* cultivar YFY-HS1 (US patent number PP16,746) was obtained from Yuen-Foong-Yu Biotech Co., Ltd in Taiwan. Tamarind XG oligosaccharide standards, the konjac glucomannan, the ivory nut mannan, the polygalacturonanase from *Aspergillus niger* (EC 3.2.1.15), endo-(1→4)-β-D-xylanase from rumen microorganism (EC 3.2.1.8), endo-(1→4)-β-D-mannanase from *A. niger* (EC 3.2.1.78), endo-(1→4)-β-D-glucanase from *Trichoderma* sp. (EC 3.2.1.4) and α-L-arabinosidase from *A. niger* (EC 3.2.1.55), and glucomannan assay kit were purchased from Megazyme International Ireland Ltd (Wicklow, Ireland). Pancreatic-amylase (3.2.1.1) was purchased from Sigma-Aldrich (St. Louis, Mo. 63103, USA). XG standards the XXG, XXGG, XXFG and XLFG were a gift from Dr. Philip J. Harris (University of Auckland, NZ). Concanavalin A (Con A, C5275) from *Canavalia ensiformis* (Jack bean) and Lipopolysaccharide (LPS, L6529) were obtained from Sigma Chemical Co. (Sigma, St. Louis, Mo.). Complete medium for culture of splenocytes was RPMI 1640 (GIBCO, Grand Island, N.Y.) supplemented with 10% FCS (Hyclone, Logan, Utah), 0.05 mM 2-mercaptoethanol, and 1% penicillin-streptomicin (Sigma). Sephacryl S-200 was purchased from GE Healthcare, DEAE-cellulose was purchased from Sigma-Aldrich, and dialysis membrane was purchased from SPECTRUM.

Example 2

Histochemical Analysis of Leaf and Stem Sections

Leaf and stem sections were cut using razor blade and examined histochemically. Secondary lignified cell walls were detected using the color reagent of phloroglucinol-HCl. Autofluorescence of the cell walls in UV radiation was examined using sections and isolated cell walls mounted in $H_2O$ and in 0.1 M ammonium hydroxide. Starch in cell wall and mucilage preparations were detected using potassium iodide, and proteins in were detected with Ponceau Red.

Example 3

Isolation of Cell-wall Alcohol-insoluble Residue and Mucilage

According to implementations and as illustrated in FIG. 1, the cell wall preparations were obtained, respectively, from the leaves and stems at 4° C. The proportion of tissues containing non-lignified primary cell walls was increased by cutting away the tissues that contain lignified secondary cells walls. The collected tissues (30 g) were homogenized in 50 mM HEPES-KOH buffer (pH 7.2) containing 0.05% of 2-mercaptoethanol. The homogenate was filtered through Miracloth, and washed with the same HEPES-KOH buffer. Liquid nitrogen was added and the residue ground to fine powders. Proteins released from cell were visualized by Ponceau 2R. The fine powders were then mixed with ice cold water, sonicated (1 min), centrifuged, and the supernatant was carefully removed. This procedure was repeated an additional 3 times. The pellets were recovered by filtration through Miracloth, and thoroughly washed with water and 70% ethanol until the filtrate became clear. Residues were then washed with 100% ethanol, followed by methanol and n-pentane, and dried overnight over silica gel under vacuum.

Mucilage was collected by gently scratching the surface of defrosted leaf and stem, then homogenized in 70% ethanol containing 0.05% of 2-mercaptoethanol. The homogenate was sonicated (2 min) and dialyzed against water for 24 h at 4° C. Mucopolysaccharides were then recovered by lyophilization. Deacetylation of the mucilage polysaccharides was done by treatment with alkali. In one approach, the sample was treated with 1 M NaOH in the presence of 1% $NaBH_4$ for 1 h at ambient temperature to remove acetyl groups, and suspension was then neutralized with glacial acetic acid to pH 5. Deacetylated mucilage polysaccharides were recovered by dialysis and lyophilization.

Example 4

Removal of Contaminating Starch

The dried cell wall preparation (200 mg) was suspended in 5 mM tris-maleate buffer (pH 6.9), and heated (85° C., 5 min)

to gelatinize the starch granules. After cooling to 40° C., porcine pancreatic-amylase (6300 units, Sigma) in 15 mM tris-maleate buffer (pH 6.9, 25 mL) containing 2 mM $CaCl_2$ was added, and the suspension was incubated for 1 h at 40° C. The mixture was centrifuged at 500 g, and the supernatant was removed. The pellets were suspended with 5 mM Tris-maleate, sonicated, filtered onto nylon mesh (pore size 11 μm), and washed with Milli-Q water until filtrate become clear. A small proportion of residue was tested with a drop of KI to indicate the absence of starch. The pellets of cell walls were dried on nylon mesh using solvent exchange by washing with ethanol, methanol, and n-pentane.

Example 5

Sequential Extraction of Cell Wall Polymers

The de-starched cell walls (50 mg) were fractionated by a sequence of extraction using 50 mM CDTA (pH 6.5), $Na_2CO_3$+25 mM $NaBH_4$, 1 M KOH+25 mM $NaBH_4$, and 4 M KOH+25 mM $NaBH_4$ as previously described. The remaining insoluble residue was accounted for by the α-cellulose fraction.

Example 6

Preparation of *D. huoshanense* Polysaccharide (DHPS)

Figure 2A:
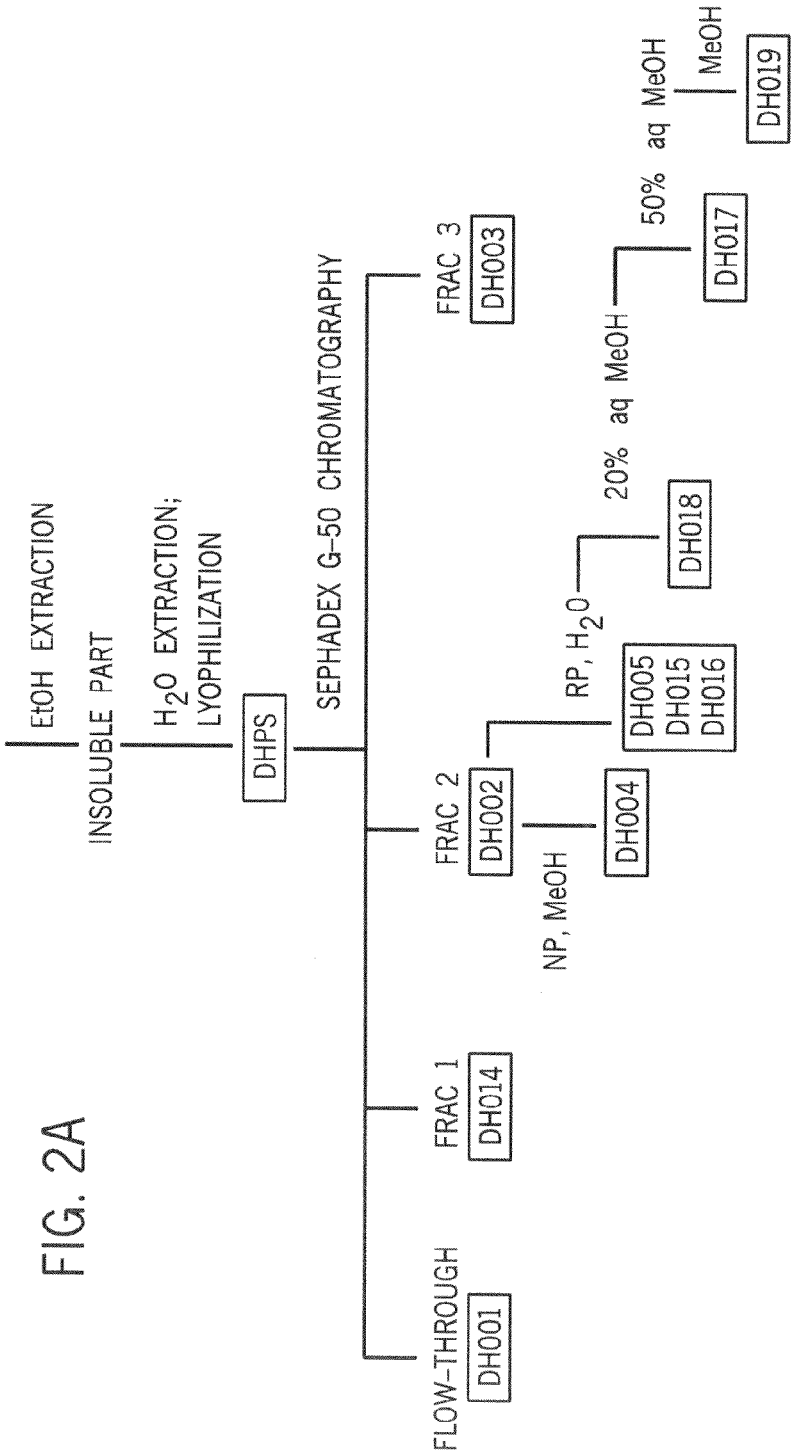
FIG. 2 is an illustration showing implementations of the preparation of DH001-DH023 for activity analysis.

According to implementations and as illustrated in FIG. 2a, the stem and leaves of *D. huoshanense* (10 g) were ground in 95% ethanol (100 mL). The mixture was filtered, and the solid portion was washed with ethanol (100 mL). The residue was stirred with cold distilled water (100 mL) at 4° C. for 1 h. The remaining pellets were removed by centrifugation (4000 rpm, 30 min), and extracted again with another portion of water (100 mL). The combined supernatant was subjected to lyophilization to give DHPS, a partially acetylated mucilage glucomannan of *D. huoshanense*.

Example 7

Preparation of DH002, DH005, and DH015-DH019

According to implementations and as illustrated in FIG. 2a, DHPS (1 g) was dissolved in distilled water (2 mL) and fractionated on a Sephadex G-50 column (2.5×60 cm) by elution with water. As illustrated in FIG. 2a, "NP" denotes normal phase, $SiO_2$ column; "RP" denotes reverse phase C18 column. The most active fraction DH002 (0.66 g) was collected, and further fractionated on a reverse-phase C18 column (2.5×20 cm) by elution with gradients of $H_2O$/MeOH (0%, 20%, 50%, and 100%). Samples DH005 and DH015-DH019 were obtained after lyophilization.

Example 8

Preparation of DH006, DH007, and DH020-DH022

Figure 2B:
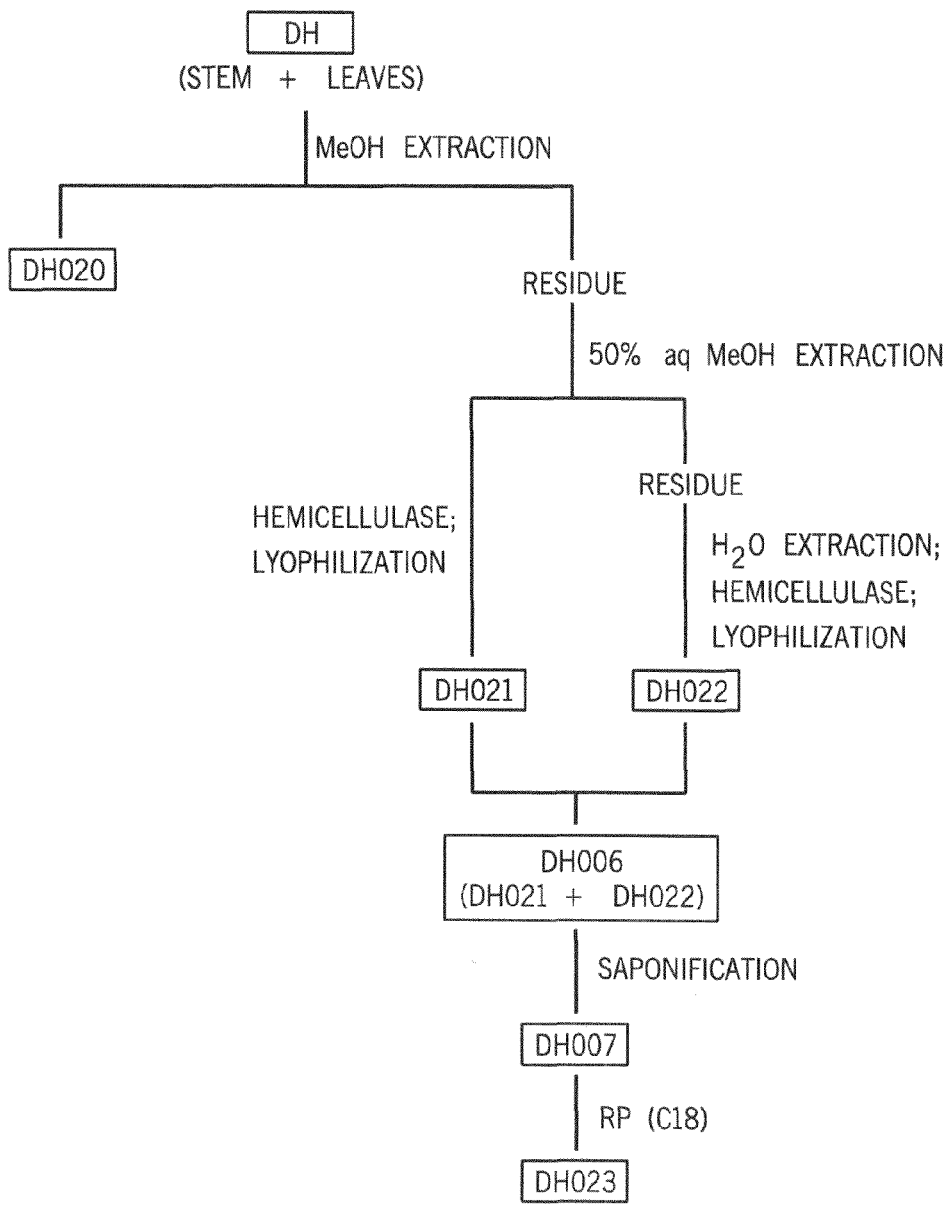

According to implementations and as illustrated in FIG. 2b, the dry DHPS powder (1 g) from the stem and leaves of *D. huoshanense* was ground in 100% MeOH (50 mL). The mixture was vortex for 30 min, and filtered by centrifugation at 3000 rpm for 10 min. This procedure was repeated twice. The supernatant was concentrated under reduced pressure to give a solid sample DH020. The residue was extracted with 50% MeOH/$H_2O$; the extract was then subjected to enzyme (hemicellulase) hydrolysis and lyophilization to give DH021. The residue was taken up by water, and subjected to enzyme (hemicellulase) hydrolysis and lyophilization to give DH022. The sample DH006 was a combination of DH021 and DH022. Saponification of DH006 with NaOH in aqueous methanolic solution at room temperature for 30 minutes gave DH007, which was purified on a reverse-phase C18 column to give DH023.

Example 9

Preparation of Man011-Man022

FIG. 3 is an illustration showing implementations of the preparation of mannose oligomers Man011-Man022 for activity analysis. The high-molecular-weight mannan was subjected to enzymatic (hemicellulase), extraction, size-exclusion (Sephadex G-10) and chromatographic separation. Saponification was conducted with NaOH in aqueous methanolic solution at room temperature for 30 minutes. Acetylation was performed with $Ac_2O$ in pyridine at room temperature for 4 hours.

Example 10

Enzymatic Hydrolysis of *D. huoshanense* Polysaccharide (DHPS)

The dried DHPS (1.6 g) was digested with hemicellulase (final concentration of 0.05%) in 100 mL distilled water for 12 h at 37° C. The reaction was stopped by boiling for 2 min. The crude mixture was centrifuged at 8000 rpm at 4° C. for 10 min. The supernatant was collected and lyophilized to give the hydrolysis product (1.47 g).

Example 11

Preparation of Bioactive Mannose Oligomer Man013

The powder of high-molecular-weight mannan (Man010, 2 g) was slightly dissolved in 100 mL of distilled water after stirring for 16 h at ambient temperature. This mixture was centrifuged at 10,000 rpm at 4° C. for 10 min, and the pellet was discarded. To the supernatant was added hemicellulase to reach a final concentration of 0.05%. The mixture was incubated at 37° C. for 12-16 h, and the enzymatic reaction was stopped by boiling for 2 min. After centrifugation (10,000 rpm, 10 min, 4° C.), the supernatant was dialyzed by membrane with MWCO of 1K daltons in water. The lyophilized oligomannoside Man013, estimated to contain 5-10 degrees of polymerization by MS analysis, was stored at 4° C. before use.

Example 12

Deacetylation of Oligo- and Polysaccharides

The oligo- and polysaccharide from *D. huoshanense* or mannan was treated with stoichiometric amounts of NaOH (or MeONa) in distilled water at ambient temperature for 30 min. The saponification product was subjected to purification, e.g. on a reverse-phase C18 column, and lyophilized to give the desired deacetylated oligo- and polysaccharides such as DH007 and Man020.

Example 13

Acetylation of Oligo- and Polysaccharides

An oligosaccharide of mannan was stirred with proper amounts of acetic anhydride in pyridine, depending on the anticipated theoretical degree of acetylation (10%, 20%, up to 100%), for 4 h at ambient temperature. The mixture was concentrated under reduced pressure, and the acetylation products were subjected to purification, e.g. on a reverse-phase C18 column, and lyophilized to give the desired (partial) acetylated oligosaccharides.

Example 14

Neutral Monosaccharide Composition of Cell Walls and Mucilage

The de-starched cell wall preparation (10 mg) or individual cell-wall fraction (5 mg) or mucilage preparation (5 mg) were hydrolyzed, respectively, with 4 M trifluoroacetic acid (TFA) at 121° C. for 1 h. The mixture was cooled, and TFA was removed under reduced pressure. The acid hydrolysate was washed with 50% aqueous methanol, and then dried in vacuo. Reduction of monosaccharides in the hydrolysate was carried out by using $NaBH_4$ (80 mg) in MeOH at room temperature for 30 min. This procedure was repeated for 3-5 times to assure complete reduction of monosaccharides to alditols. The mixture was washed with concentrated HCl and MeOH, and then dried in vacuo. The reduction product of alditols was subjected to acetylation using acetic anhydride in pyridine (1:2) at 80° C. for 2 h, followed by incubation at 25° C. for 16 h. The alditol peracetates were extracted by chloroform/2 M HCl (2:1), and washed carefully with saturated $NaHCO_3$. After removal of chloroform, the composition of alditol peracetates was determined by GC-MS analysis.

Example 15

Linkage Analysis of the Cell-wall Polysaccharides

Each cell-wall fraction (10 mg) was dissolved in DMSO (2 mL), treated with NaH for 2 min with continuous stirring, and ice cold MeI (1 mL) was added. After stirring at room temperature for 16 h, the methylated polysaccharides in suspension were separated by addition of chloroform/water (2:1). The organic phase was washed with 10% $Na_2S_2O_3$ and water, and then concentrated under reduced pressure to give the crude product of methylated polysaccharides. The IR and $^1H$ NMR analyses indicated no presence of hydroxyl group. According to the above-described procedure, the product of methylated polysaccharides was similarly digested with TFA, reduced with $NaBH_4$, and acetylated with $Ac_2O$/pyridine to give methylated alditol peracetates. The composition of methylated alditol peracetates was determined by GC-MS analysis.

Example 16

Uronic-acid Composition of Cell Walls and the Cell-wall Fractions

Using m-hydroxyl diphenyl as the chromogen, the total content of uronic acids in cell walls and each cell-wall fraction was determined according to the previously reported method. Galacturonic acid (GalA), glucuronic acid (GlcA) and 4-O-methylglucuronic acid (MeGlcA) in acid hydrolysates were separated and quantified by HPAEC-PAD (Dionex, Sunnyvale, Calif., USA) on a CarboPAC-1 column eluted with isocratic gradient of 150 mM NaOAc containing 100 mM NaOH at a flow rate of 0.25 mL $min^{-1}$.

Example 17

Enzyme Hydrolysis

The polysaccharide fractions were treated with different enzymes to release oligosaccharides for further analysis. Enzymatic reactions were stopped by boiling for 2 min. The CDTA fractions (2 mg) of leaf and stem wall fractions were treated with polygalacturonase (50 U) from *A. niger* (EC 3.2.1.15) with 100 mM NaOAc (pH 4.0, 200 μL) for 16 h at 50° C. The 1 M KOH fractions (2 mg) of leaf and stem wall preparations were treated with endo-(1→4)-β-D-xylanase (45 U, EC 3.2.1.8) with 100 mM NaOAc (pH 6.0, 200 μL) for 1 h at 60° C. The 4 M KOH fractions (2 mg) of leaf and stem wall preparations were treated with endo-(1→4)-β-D-glucanase (EC 3.2.1.4, 5 U) with 50 mM ammonium formate (pH 5.0, 200 μL) for 16 h at 37° C. The arabinosyl residues were removed from xylo-oligosaccharides in xylanase digest (1 M KOH fraction of wall preparations) by treatment of α-L-arabinosidase from *A. niger* (EC 3.2.1.55), and endo-(1→4)-β-D-xylanase digest was freeze dried, redissolved with 100 mM NaOAc (pH 6), followed by incubation with α-L-arabinosidase (10 U) at 40° C. for 24 h.

The stem mucilage preparation was treated with endo-(1→4)-β-D-mannase (EC 3.2.1.78, 5 U) with 100 mM NaOAc (pH4, 200 μL) for 16 h at 40° C. The deacetylated glucomannan of fraction B was digested with endo-β-1,4-mannase (*A. niger*, Megazyme) in sodium acetate buffer (100 mM. pH 4.5) for 24 h at 37° C., using 5 μL enzyme per 1 mg of deacetylated glucomannan. Digestion with β-mannosidase that was specific for β-1,4-mannosyl linkage (*C. fimi*, Megazyme) was conducted in sodium maleate buffer (100 mM. pH 6.5) for 24 h at 37° C., using 5 μL enzyme per 1 mg of deacetylated glucomannan. The attempted digestion with α-1,2,3,6-mannosidase (Jack bean, Sigma) was performed in ammonia acetate buffer (50 mM, +1 mM $ZnCl_2$, pH 5.5) for 24 h at 37° C., using 5 μL enzyme per 1 mg of deacetylated glucomannan.

Example 18

GC-MS Analysis

The alditol acetates and partially methylated alditol acetates were separated by BPX-70 column (SGE Analytical Science Pty Ltd., Victoria 3134, Australia) on PolarisQ Ion Trap GC-MS/MS System (Thermo Fisher Scientific, Inc, Waltham, Mass. 024253, USA). Oven temperature was increased from 38° C. to 150° C. at 50° C. per min, then to 230° C. at 3° C. per min and to 260° C. for 5 min, with carrier gas (He) at a flow rate of 1 mL/min. Quantification was done by correcting peak area to mol %.

Example 19

HPAEC-PAD Analysis

According to implementations, FIG. 8 illustrates data of a HPAEC-PAD chromatogram (left panel) of XG oligosaccharides released from the 4 M KOH fraction of *D. huoshanense* leaf cell-wall preparation with treatment of endo-(1→4)-β-D-glucanase. The peak assignment was based on the retention times of the XG oligosaccharide standards. G: Glc; X: Xyl-Glc; L: Gal-Xyl-Glc; F: Fuc-Gal-Xyl-Glc; DH-Ac is also referred to as DH023.

XG oligosaccharides were separated and characterized by HPAEC-PAD with known standards, using a Dionex BioLC system (Dionex, Sunnyvale, Calif., USA). A CarboPac PA1 analytical column (4 mm×250 mm) and a CarboPac PA1 guard column (4 mm×50 mm) were used. The XG oligosaccharides were separated using a linear gradient of 50 mM NaOAc+100 mM NaOH (solvent A) to 100 mM NaOAc+100 mM NaOH (solvent B) at 1 mL/min over 110 min. After each run, the column was washed for 10 min with solvent B, 5 min with 300 mM NaOH (solvent C), and 30 min with solvent A.

Example 20

Mass Spectrometry

Figure 9A:
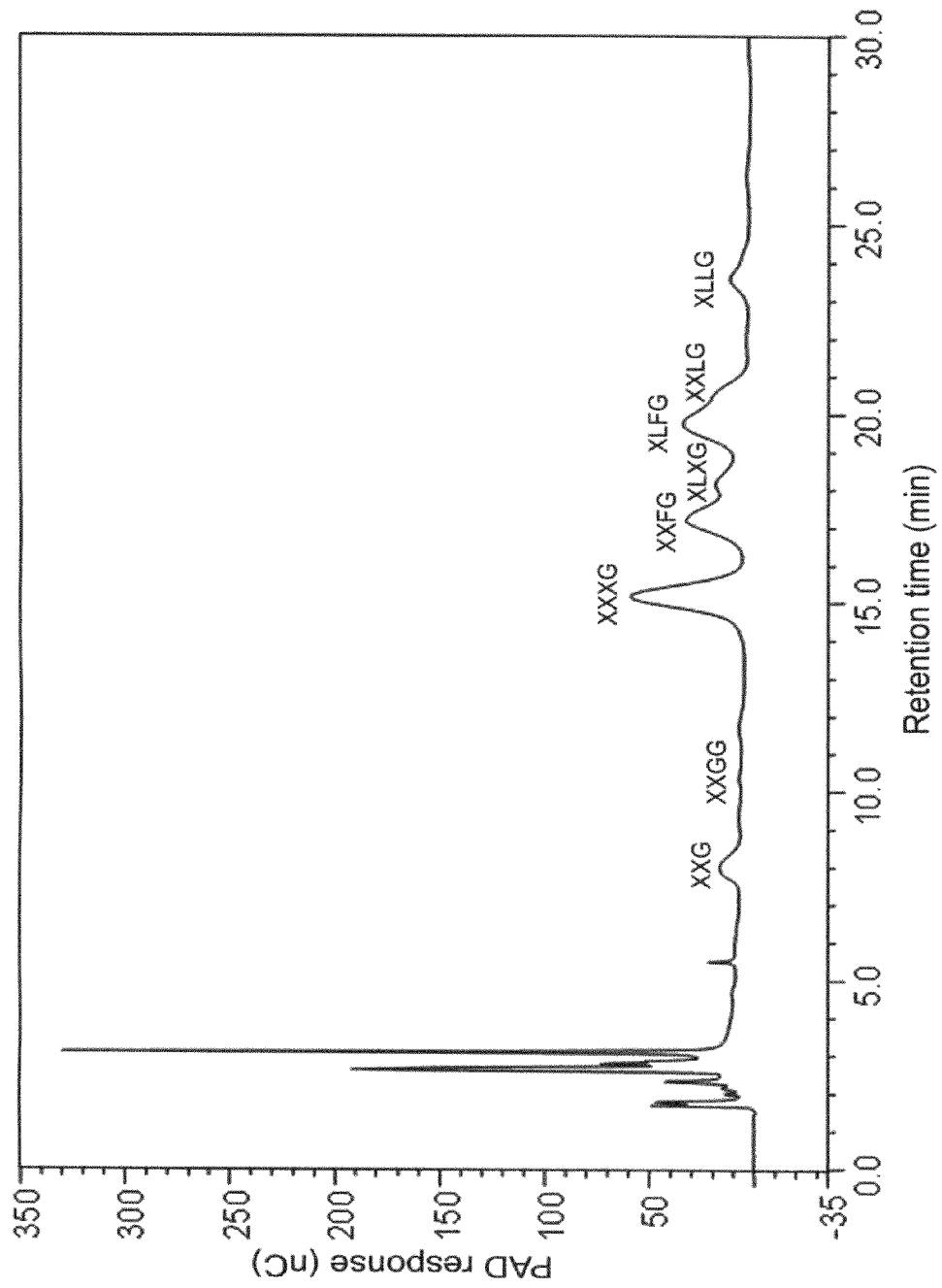
FIG. 9 are graphs showing implementations of illustrative data of a HPAEC-PAD chromatogram (left panel) and a MALDI-TOF MS spectrum (right panel) of XG oligosaccharides released from the 4 M KOH fraction of *D. huoshanense* leaf cell-wall preparation with treatment of endo-(1→4)-β-D-glucanase.
Figure 9B:
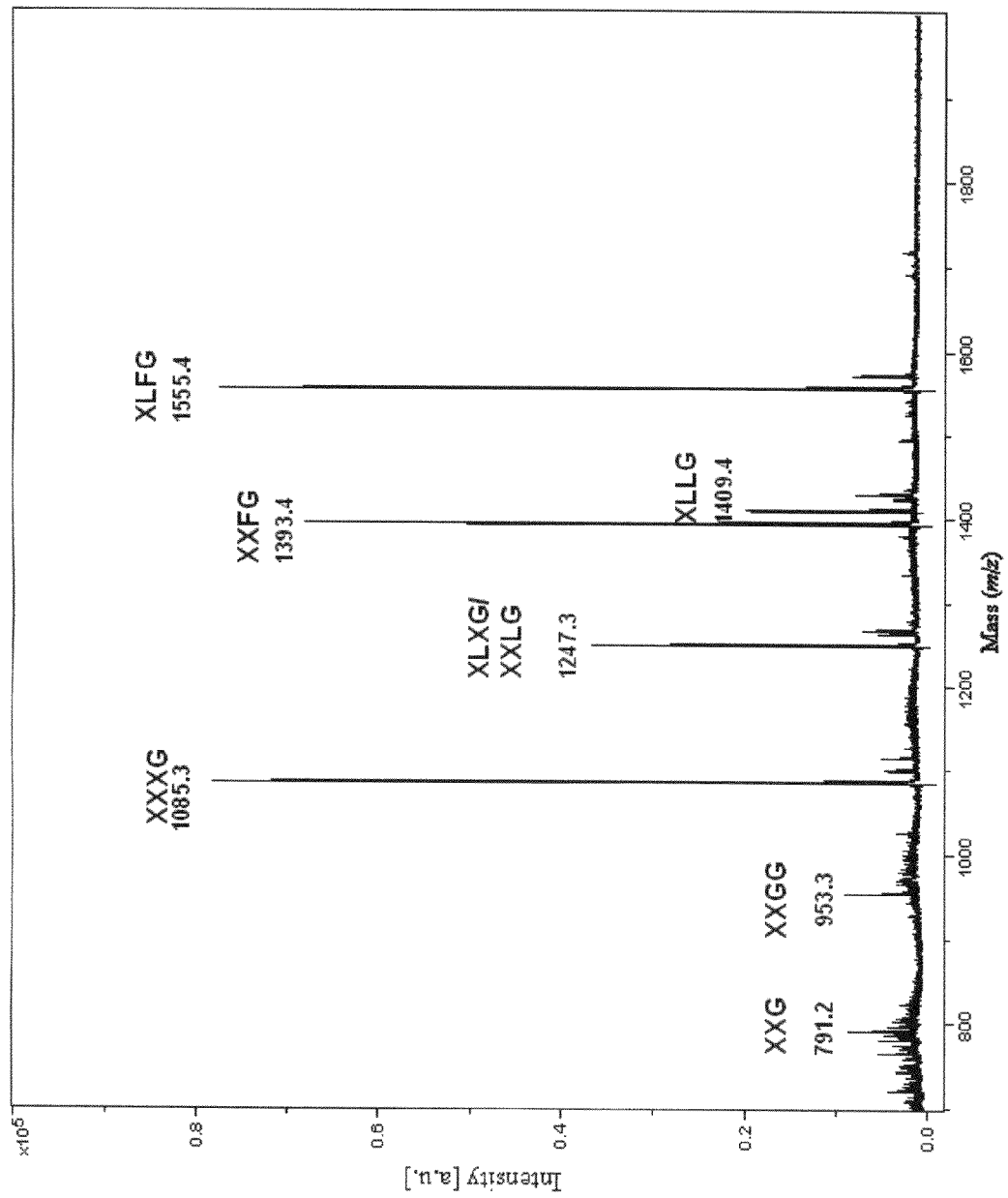

According to implementations, FIG. 9 illustrates data of a MALDI-TOF MS spectrum (right panel) of XG oligosaccharides released from the 4 M KOH fraction of *D. huoshanense* leaf cell-wall preparation with treatment of endo-(1→4)-β-D-glucanase. The peak assignment was based on the retention times of the XG oligosaccharide standards. G: Glc; X: Xyl-Glc; L: Gal-Xyl-Glc; F: Fuc-Gal-Xyl-Glc.

The molecular weights of the sodium adducts of oligosaccharides [M+Na]$^+$ were determined using a BioTOF Ultraflex II (Bruker Daltonics, Billeriaca, Mass. 01821, USA). The enzyme hydrolysate containing oligosaccharides were mixed with 10 mM of 2,5-dihydroxybenzoic acid and 10 mM NaCl in the ratio of 5:5:3. In MS mode, the spectra were accumulated in average of 2000-3000 shuts.

According to implementations, FIG. 19 illustrates an exemplary mass spectrum of an oligomannose containing 66% (Man)$_6$+34% (Man)$_n$ (n≧7).

Example 21

NMR Spectral Analysis

The NMR spectra were recorded on Bruker ADVANCE 600 MHz NMR spectrometer (Bruker BioSpin GmbH, Rheinstetten, Germany) with 5 mm Cryoprobe DCI $^1$H/$^{13}$C. Samples were dissolved in 1 mL of D$_2$O. Chemical shifts are given in δ values relative to HOD signal ($\delta_H$ 4.8 at 25° C.) or the H-1/C-1 signals of mannopyranose ($\delta_H$ 4.71/$\delta_C$ 100.6). The HSQC spectra were recorded at 50° C. to shift the HOD peak about 0.2 ppm upfield, so that the obscured signals in the (1→4)-linked unacetylated β-Manp residues were revealed. ROESY and TOCSY spectra were recorded, respectively, with mixing times of 100 and 70 ms as well as the relaxation delays of 3 and 2 s.

According to implementations, FIG. 13 is an $^1$H NMR spectrum of the polysaccharide of fraction B in D$_2$O shows the ratio of Manp/2-O-AcManp/3-O-AcManp=66:19:15.

Figure 21:
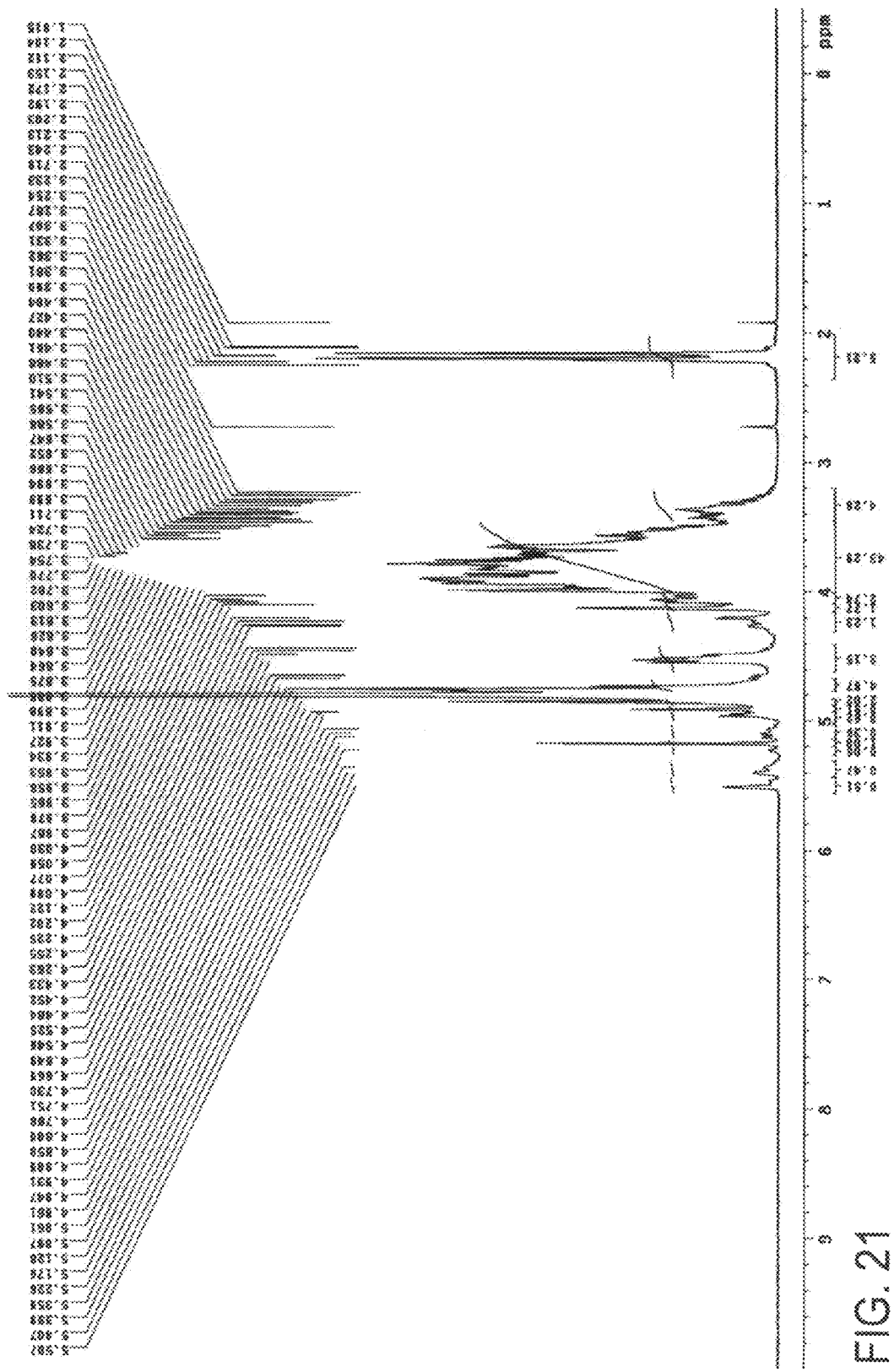
FIG. 21 is a graph of an implementation of an $^1$H NMR of sample DH018 prepared from *D. huoshanense* (400 MHz, $D_2O$)
Figure 22:
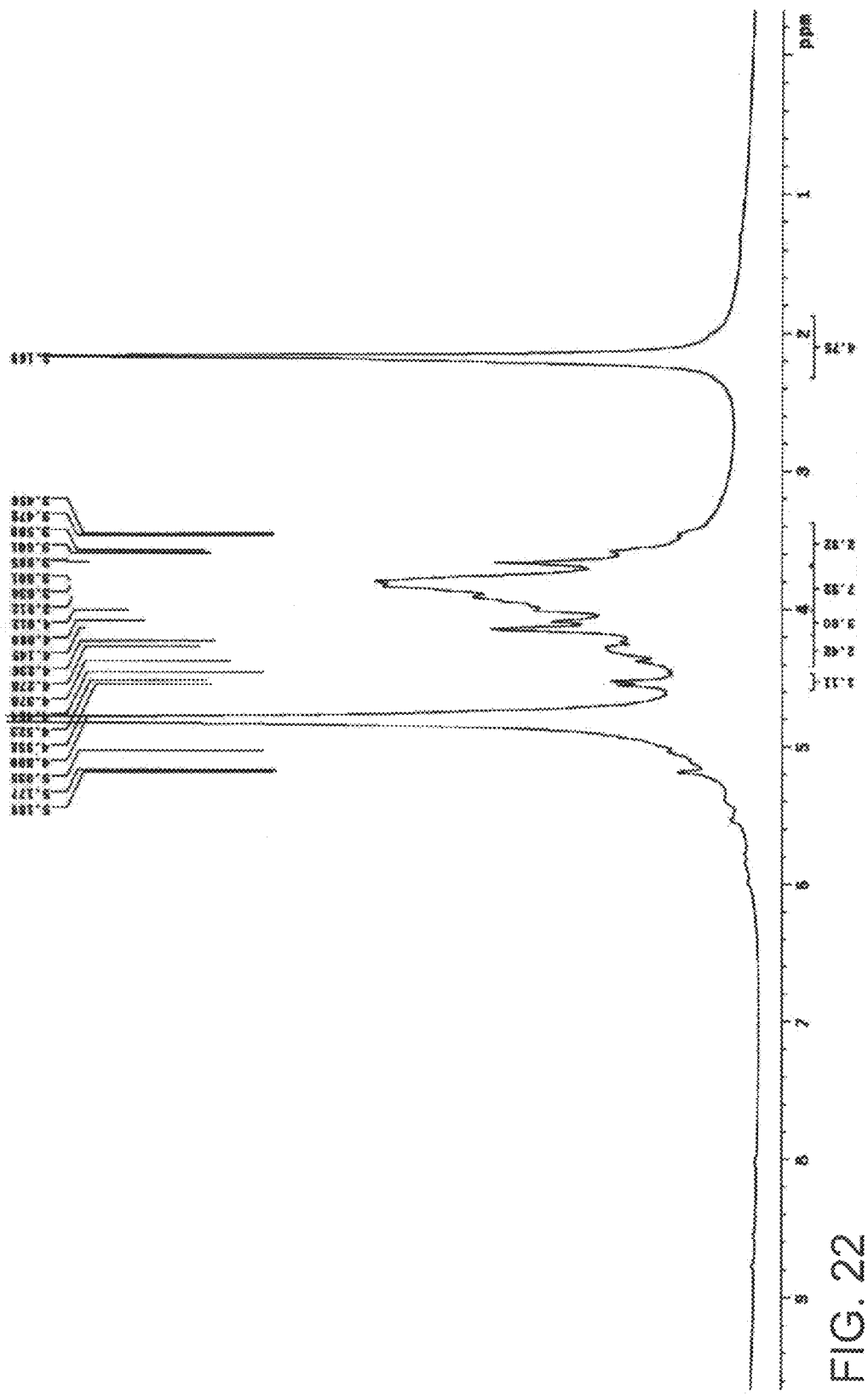
FIG. 22 is a graph of an implementation of an $^1$H NMR of a partially acetylated oligomannose Man018 (400 MHz, $D_2O$)
Figure 23:
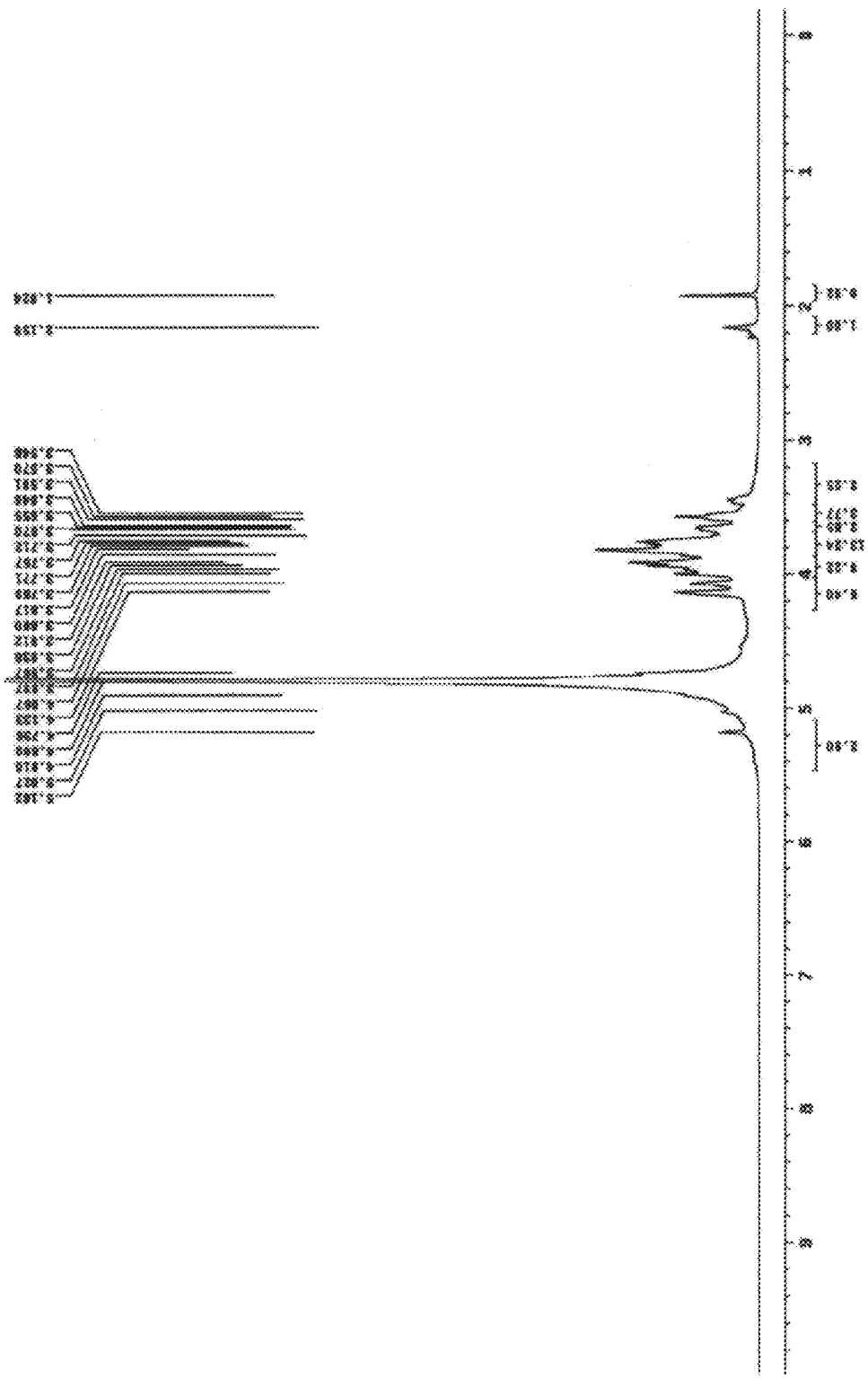
FIG. 23 is a graph of an implementation of an $^1$H NMR of oligomannose Man020 (400 MHz, $D_2O$).

According to implementations, FIG. 21 shows an exemplary $^1$H NMR of sample DH018 prepared from *D. huoshanense* (400 MHz, D$_2$O). FIG. 22 shows an exemplary $^1$H NMR of a partially acetylated oligomannose Man018 (400 MHz, D$_2$O). FIG. 23 shows a $^1$H NMR of oligomannose Man020 (400 MHz, D$_2$O).

Example 22

Correlative NMR

According to implementations using correlative analysis, FIG. 17 are graphs of illustrative data of heteronuclear multiple bond correlation (HMBC) spectra of fraction B. Panel (a) shows the cross-peaks in the region of δ 5.55-4.45, and panel (b) shows the cross-peaks in the region of δ 4.30-3.30. Cross-peaks 1, H-2(Man)/C-3(Man); 2, H-2(Man$_{34}$)/C-3 (Man$_{34}$); 3, H-4(Man$_{34}$)/C-5(Man$_{34}$); 4, H-2(Man)/C-4 (Man); 5, H-4(Man$_{34}$)/C-3(Man$_{34}$); 6, H-3(Man$_{24}$)/C-5 (Man$_{24}$); 7, H-4(Man$_{24}$)/C-3(Man$_{24}$); 8, H-4(Man)/C-3 (Man); 9, H-3(Man$_{24}$)/C-2(Man$_{24}$); 10, H-4(Man)/C-5 (Man); 11, H-3(Man)/C-4(Man); 12, H-4(Glc)/C-3(Glc); 13, H-3(Glc)/C-4(Glc); 14, H-5(Man$_{34}$)/C-4(Man$_{34}$); 15, H-2 (Glc)/C-3(Glc). All the saccharides were linked in the backbone by β-(1→4) linkage. Man$_{24}$ represents 2-O-acetylated Man, and Man$_{34}$ represents 3-O-acetylated Man.

According to implementations, FIG. 18 illustrates data of a rotational nuclear overhauser effect spectroscopy (ROESY) spectrum of fraction B, which shows the intra- and inter-glycosidic correlations (indicated by quotation marks) in the glucomannan.

Example 23

HPSEC Analysis

According to implementations, FIG. 14 illustrates data from a refractive-index profile of HPSEC analysis of the polysaccharides in fraction B on the SEC-1000 column (panel a) and G-3000 column (panel b).

Example 24

Determination of Molecular Weight by DOSY

The sample of fraction B (1 mg) was dissolved in 400 μL of D$_2$O, and the average molecular weight of the polysaccharide components was determined by DOSY. The values of hydrodynamic radii were determined from pullulan standards. The DOSY experiment was carried out using a stimulated echo sequence incorporating bipolar sine gradient pulses. In addition, the HOD signal was suppressed by means of presaturation. The gradient strength was logarithmically incremented in 32 steps from 2% up to 95% of the maximum gradient strength. The diffusion time was set between 100 and 700 ms. Gradient pulse and longitudinal eddy current were set to 3 ms and 25 ms, respectively.

According to implementations, FIG. 15 is a graph of illustrative data of a DOSY spectroscopy of fraction B. The molecular weight of 9.7 KDa was deduced from the equation D=8.2×10$^{-9}$ MW$^{-0.50}$ (m$^2$ s$^{-1}$) with the diffusion coefficient of −10.08.

Example 25

Fraction B Glycan Structure

According to implementations, FIG. 19 illustrates data of a tentative partial structure of the polysaccharide in fraction B.

Example 26

Preparation of SpMC (Murine Spleen Mononuclear Cell)

Six-to-eight week old male Balb/c were purchased from National Laboratory Animal Center (Taipei, Taiwan) and were sacrificed by cervical dissociation. Mice splenocytes were obtained by pressing spleens through a sterilized stainless steel mesh (100 mesh) and washing the passed suspension 3 times with HBSS (GIBCO) after depleting erythrocytes with Red blood Cell lysis buffer (Sigma). Finally, the viable cells were counted with a hemocytometer using trypan blue dye exclusion. Single-cell suspensions ($5\times10^6$ cells per mL) were cultured in 10% RPMI-1640 in a humidified 5% $CO_2$ incubator at 37° C.

Example 27

Cytotoxicity/Proliferation Assay

Mice splenocytes ($5\times10^5$ cells per well) were stimulated directly with Con A (2 μg/mL), commercial mannan analogs (konjac glucomannan and ivory nut mannan) or different polysaccharide fractions (50 μg/mL) in 96-well tissue culture plates for 60 h. Afterwards, the cell proliferation was examined with MTS assay using Celltiter 96® aqueous one solution cell proliferation assay kit (Promega, Madison, Wis.) following manufacturer's instructions. Briefly, 20 μL of MTS solution was added to each well. After 4 h incubation at 37° C., the absorbance at 490 nm was obtained using a plate reader (SpectraMax M2, Molecular Device, Sunnyvale, Calif.). The optical density at 490 nm ($OD_{490}$) for control cells were defined as 100%. Polysaccharide preparation is screened routinely with LAL test (Pyrochrome® Kit, Cape Cod Associates, Falmouth, Mass.) to ensure no endotoxin contamination. The endotoxin potency (EU/mg) of each polysaccharide fractions ($\leq1\times10$ EU/mg) was shown in much lower level than that of cell culture with lipopolysaccharide (LPS$\geq1\times10^5$ EU/mg).

Example 28

Cytokine Determination by ELISA

The concentrations of IL-1α, IL-6, IL-10, IFN-γ, G-CSF and GM-CSF in the cell culture supernatants were assayed using the Quantikine mouse ELISA kits (R&D Systems, Minneapolis, Minn.) according to the manufacturer's protocol. Mice splenocytes ($5\times10^6$ cells/well) were cultured in the presence of mannan, glucomannan, or different polysaccharide fractions at concentration of 50 μg/mL in 24-well tissue culture plates. Con A at a final concentration of 2 μg/mL were used as a positive control. After 48 h following stimulation, culture supernatants were collected and stored at −80° C. until ELISA analysis. In this study, all of the data points are average from three independent experiments and the represented values are average ± standard deviation.

Example 29

Cytokine Expression Inferred from the RT-PCR Assessment

Splenocytes were removed from BALB/c mice (male, 6-8 weeks) and treated with fractions A-F (100 μg/mL each) for 12 h. Both the cell pellets and supernatants were collected at the end of the incubation period. RNA was extracted from cell pellets and converted to cDNA. Products from PCR were analyzed by gel electrophoresis on 2% gel to visualize the expressed cytokines.

Example 30

RT-PCR Assessment of Cytokines

According to implementations illustrated in FIG. 4, there is shown a graph of illustrative data of assessment of cytokines (IFN-γ, TNF-α, IL-10, G-CSF, GM-CSF, and M-CSF) by RT-PCR on cultured mice macrophage RAW264.7 cells with different samples for 12 hours. The contents of each lane are as follows: Lane 1, untreated cells; lane 2, Con A (4 μg/ml); lane 3, crude extract of D. huoshanense polysaccharide (DHPS, 100 μg/ml); lane 4, 1,4-β-D-mannobiose ((Man)$_2$, 100 μg/ml); lane 5, 1,4-β-D-mannotriose ((Man)$_3$, 100 μg/ml); lane 6, 1,4-β-D-mannotetraose ((Man)$_4$, 100 μg/ml); lane 7, 1,4-β-D-mannopentaose ((Man)$_5$, 100 μg/ml); lane 8, 1,4-β-D-oligomannose mixture containing 66% (Man)$_6$+ 34% (Man)$_n$ (n$\geq$7, 100 μg/ml); lane 9, galactosyl-mannobiose (100 μg/ml); lane 10, galactosyl-mannotriose (100 μg/ml); lane 11, di-galactosyl-mannopentaose (100 μg/ml).

Example 31

Assessment of G-CSF

According to implementations and as shown in FIG. 5, G-CSF is assessed by RT-PCR on mice splenocytes with different samples for 12 hours. Lane 1, untreated cells; lane 2, Con A (4 μg/ml); lane 3, crude extract of D. huoshanense polysaccharide (DHPS, 100 μg/ml); lane 4, 1,4-β-D-mannobiose ((Man)$_2$, 100 μg/ml); lane 5, 1,4-β-D-mannotriose ((Man)$_3$, 100 μg/ml); lane 6, 1,4-β-D-mannotetraose ((Man)$_4$, 100 μg/ml); lane 7, 1,4-β-D-mannopentaose ((Man)$_4$, 100 μg/ml); lane 8, 1,4-β-D-oligomannose mixture containing 66% (Man)$_6$+34% (Man)$_n$ (n$\geq$7, 100 μg/ml); lane 9, galactosyl-mannobiose (100 μg/ml); lane 10, galactosyl-mannotriose (100 μg/ml); lane 11, di-galactosyl-mannopentaose (100 μg/ml).

According to implementations, FIG. 6 is a data of assessment of G-CSF expression of the protein level. Mice macrophage RAW264.7 cells were treated with individual samples for 12 hours. The medium was harvested and analyzed for G-CSF production using an ELISA kit. The following are the lane descriptions: Lane 1, untreated cells; lane 2, crude extract of D. huoshanense polysaccharide (DHPS, 100 μg/ml); lane 3, 1,4-β-D-mannobiose ((Man)$_2$, 100 μg/ml); lane 4, 1,4-β-D-mannotriose ((Man)$_3$, 100 μg/ml); lane 5, 1,4-β-D-mannotetraose ((Man)$_4$, 100 μg/ml); lane 6, 1,4-β-D-mannopentaose ((Man)$_4$, 100 μg/ml); lane 7, 1,4-β-D-oligomannose mixture containing 66% (Man)$_6$+34% (Man)$_n$ (n$\geq$7, 100 μg/ml); lane 8, galactosyl-mannobiose (100 μg/ml); lane 9, galactosyl-mannotriose (100 μg/ml); lane 10, di-galactosyl-mannopentaose (100 μg/ml).

According to implementations, FIG. 7 illustrates the dose- and time-dependent response of a mannose oligomer on the production of G-CSF. The left panel shows mice macrophage RAW264.7 cells that were treated with various concentration of 1,4-β-D-oligomannose (1-50 μg/ml) containing 66% (Man)$_6$+34% (Man)$_n$ (n$\geq$7) for 6 hours. The medium was harvested and analyzed for G-CSF production using an ELISA kit. The right panel shows mice macrophage RAW264.7 cells treated with 30 μg/ml of 1,4-β-D-mannose oligomer containing 66% (Man)$_6$+34% (Man)$_n$ (n$\geq$7) for 0-3 hours. After treatment, the cells were processed for RT-PCR detection of G-CSF gene expression.

According to implementations, FIG. 8 illustrates data assessment of the protein level of G-CSF expression. Mice macrophage RAW264.7 cells were treated with the representative samples for 12 hours. The medium was harvested and analyzed for G-CSF production using an ELISA kit. The most potent sample Man013 was obtained from Man010 (a mannan with average of 15 DP) by enzymatic (hemicellulase) hydrolysis, dialysis (molecular-weight cut-off=1000), and chromatography on a Sephadex G-10 column.

According to implementations, FIG. 11 illustrates data of dose-response relationships of mucilage polysaccharide on the production of cytokines and hematopoietic growth factors. Mice splenocytes ($5 \times 10^6$ cells) were stimulated with Con A (2 μg/mL) or stem mucilage polysaccharide (2-250 μg/mL). After 48 h incubation, cell culture supernatant was harvested and analyzed for (a) G-CSF and (b) GM-CSF production using the ELISA kits.

While the apparatus and method have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:

1. A composition comprising:
   an extract of *Dendrobium huoshanense* mucilage prepared by a method comprising subjecting the mucilage to (a) anion-exchange chromatography followed by (b) size-exclusion chromatography and selection of a fraction B based on an ability to induce cytokine expression;
   wherein the fraction B comprises at least one acetylated polysaccharide of formula:
   Fraction B

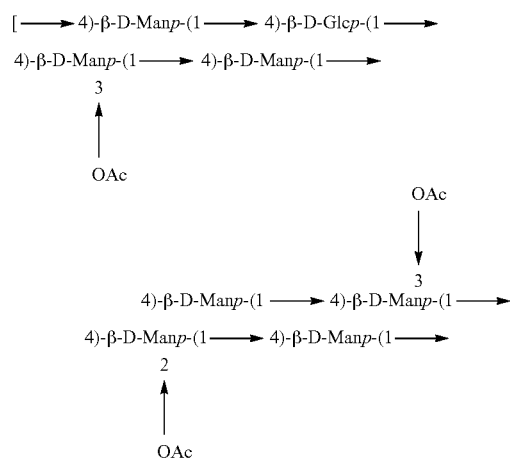

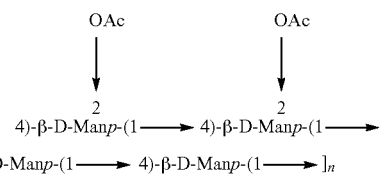

in an amount sufficient to upregulate beneficial proteins in a subject.

2. The composition of claim 1, wherein the proteins comprise growth factors.

3. The composition of claim 1, wherein the proteins comprise cytokines.

4. The composition of claim 1, wherein the at least one acetylated polysaccharide comprise those listed in Table 1.

5. The composition of claim 1, wherein the number of monosaccharides in the polysaccharide (degree of polymerization) is greater than 6.

6. The composition of claim 1, wherein the Fraction B contains β-(1→4)glucomannan having partial acetylation at 2- and 3-positions of mannosides.

7. A pharmaceutical composition comprising:
   the composition of claim 1 and a pharmaceutically acceptable carrier.

8. The composition of claim 7, wherein the composition is suitable to be administrated orally.

9. The composition of claim 7, wherein the composition is suitable for injection.

10. The composition of claim 7, wherein the composition effects the increase of beneficial cytokines selected from IFN-γ, IL-10, IL-6 and IL-1α.

11. The composition of claim 10, wherein the cytokine is selected from GM-CSF and G-CSF.

* * * * *